US010125099B2

(12) United States Patent
Shih et al.

(10) Patent No.: US 10,125,099 B2
(45) Date of Patent: Nov. 13, 2018

(54) MAO INHIBITORS AND THEIR CONJUGATES AS THERAPEUTICS FOR THE TREATMENT OF BRAIN CANCER

(71) Applicant: UNIVERSITY OF SOUTHERN CALIFORNIA, Los Angeles, CA (US)

(72) Inventors: Jean C. Shih, Beverly Hills, CA (US); Florence M. Hoffman, Venice, CA (US); Thomas C. Chen, La Canada Flintridge, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/293,055

(22) Filed: Oct. 13, 2016

(65) Prior Publication Data

US 2017/0029371 A1 Feb. 2, 2017

Related U.S. Application Data

(60) Division of application No. 14/615,416, filed on Feb. 5, 2015, now Pat. No. 9,675,620, which is a continuation-in-part of application No. 13/559,431, filed on Jul. 26, 2012, now Pat. No. 9,771,625.

(60) Provisional application No. 61/937,425, filed on Feb. 7, 2014, provisional application No. 61/511,920, filed on Jul. 26, 2011.

(51) Int. Cl.
| | |
|---|---|
| C07D 209/14 | (2006.01) |
| A61K 31/405 | (2006.01) |
| A61K 31/4045 | (2006.01) |
| A61K 31/137 | (2006.01) |
| A61K 49/16 | (2006.01) |
| A61K 31/135 | (2006.01) |
| A61K 31/138 | (2006.01) |
| A61K 31/366 | (2006.01) |
| A61K 31/15 | (2006.01) |
| A61K 31/495 | (2006.01) |
| A61K 31/357 | (2006.01) |
| A61K 31/352 | (2006.01) |
| A61K 31/381 | (2006.01) |
| C12N 15/113 | (2010.01) |
| A61K 31/4188 | (2006.01) |
| A61K 31/5375 | (2006.01) |
| C07D 209/24 | (2006.01) |
| A61K 45/06 | (2006.01) |

(52) U.S. Cl.
CPC .......... *C07D 209/14* (2013.01); *A61K 31/135* (2013.01); *A61K 31/137* (2013.01); *A61K 31/138* (2013.01); *A61K 31/15* (2013.01); *A61K 31/352* (2013.01); *A61K 31/357* (2013.01); *A61K 31/366* (2013.01); *A61K 31/381* (2013.01); *A61K 31/405* (2013.01); *A61K 31/4045* (2013.01); *A61K 31/4188* (2013.01); *A61K 31/495* (2013.01); *A61K 31/5375* (2013.01); *A61K 45/06* (2013.01); *A61K 49/16* (2013.01); *C07D 209/24* (2013.01); *C12N 15/1137* (2013.01); *C12Y 104/03004* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 7,056,952 | B1 | 6/2006 | Joannou |
| 7,344,699 | B2 | 3/2008 | Lappin et al. |
| 7,799,955 | B2 | 9/2010 | Joannou |
| 2005/0222248 | A1 | 10/2005 | Joannou |
| 2008/0125481 | A1 | 5/2008 | Joannou |
| 2009/0209655 | A1 | 8/2009 | Joannou |
| 2010/0048921 | A1 | 2/2010 | Gorne |
| 2010/0137425 | A1 | 6/2010 | Bergan et al. |
| 2010/0143295 | A1 | 6/2010 | Gant et al. |
| 2010/0273891 | A1 | 10/2010 | Joannou |
| 2010/0290997 | A1 | 11/2010 | Li et al. |

FOREIGN PATENT DOCUMENTS

| | | |
|---|---|---|
| DE | 102007002386 A1 | 7/2008 |
| WO | 0066576 A1 | 11/2000 |
| WO | 2009012109 A2 | 12/2009 |
| WO | 2009152440 A1 | 12/2009 |
| WO | 2010042933 A2 | 4/2010 |
| WO | 2011116142 A1 | 9/2011 |
| WO | 2012018761 A2 | 2/2012 |
| WO | 2013016580 A2 | 1/2013 |

(Continued)

OTHER PUBLICATIONS

International Preliminary Report on Patentability dated Aug. 9, 2016 issued in counterpart International Application No. PCT/US2015/014695.

(Continued)

*Primary Examiner* — Thor Nielsen
(74) *Attorney, Agent, or Firm* — DLA Piper LLP (US)

(57) ABSTRACT

A pharmaceutical composition and method for treating brain cancer are provided. The method includes administering to a patient in need thereof an effective amount of one or more compounds that include moclobemide, clorgyline, clorgyline's Near-infra-red dye Monoamine Oxidase Inhibitor (NMI), and MHI 148-clorgyline, and their salt thereof. The composition and method are particularly effective in reducing the size of glioblastomas that are temozolomide (TMZ) resistant.

4 Claims, 36 Drawing Sheets

(21 of 36 Drawing Sheet(s) Filed in Color)

(56) References Cited

FOREIGN PATENT DOCUMENTS

| WO | WO 2013/033688 A1 | 3/2013 |
|---|---|---|
| WO | 2014018563 A2 | 1/2014 |

OTHER PUBLICATIONS

European Search Report (Communication pursuant to Rule 164(2)(b) and Article 94(3) EPC) dated Jul. 21, 2015 issued in corresponding EPC Application No. 12748805.4.
Yang et al., Clinical Cancer Research 16(10) p. 2833-2844, May 15, 2010.
Gao et al., Nature Biotechnology 22(6), p. 969-976, 2004.
Samia et al., JACS 125(51), p. 15736-15737, 2003.
Kukowska-Latallo et al., Cancer Research 65(12) p. 5317-5324, 2005.
Lee et al., Journal of Organic Chemistry, vol. 73, p. 723-725, 2008.
International preliminary report on patentability dated Aug. 13, 2013 issued in corresponding PCT application PCT/US2012/048407.
International Search Report and Written Opinion dated Feb. 13, 2013 issued in corresponding PCT application PCT/US2012/048407.
Peehl et al., Journal of Urology, vol. 180, p. 2206-2211, 2008.
Flamand et al., European Urology Supplements, vol. 9(2), p. 274, 2010.
Flamand et al., Journal of Cancer Research and Clinical Oncology, vol. 136, p. 1761-1771, 2010.
Zhao et al., BMC Medical Genomics, vol. 2, p. 1-15, 2009.
Baumanis, et al., "The modification of the catalytic activity of mitochondrial monoaminoxidase and the suppression of the growth of experimental brain tumors", Database Medline (Online): US National Library of Medicine (NLM), Bethesda, MD, US; Jul. 1990 [abstract].
Singh, et al., "Inhibition of LSD1 sensitizes glioblastoma cells to histone deacetylase inhibitors.", Neuro-Oncology, vol. 13, No. 8, Aug. 2011.
Baumanis, et al., "[comparative study of the effect of inhibitors of monoamine oxidase and ftorafur on the growth of de-differentiated astrocytoma]." Database Medline (Online); US National Library of Medicine (NLM); Bethesda, MD, US: 1976 [abstract].
Adler, et al., "Pharmacological treatment of frontotemporal dementia: treatment response to the MAO-A inhibitor moclobemide", International Journal of Geriatric Psyschiatry, vol. 18, No. 7, Jul. 1, 2003.
Jhaveri, et al., "Noscapine inhibits tumor growth in TMZ-resistant gliomas", Cancer Letters, New York, NY, US, vol. 312, No. 2, Aug. 15, 2011 [abstract].
Virrey, et al., "Glioma-associated endothelial cells are chemoresistant to temozolomide", Journal of Neuro-Oncology, Kluwer Academic Publishers, BO, vol. 95, No. 1, Apr. 18, 2009.
Gabilondo, et al., "Monoamine oxidase B activity is increased in human gliomas", Neurochemistry International, Pergamon Press, Oxford, GB, vol. 52, No. 1-2, Dec. 12, 2007.
Annex to Form PCT/ISA/206 Communication Relating to the Results of the Partial International Search issued in related International Application No. PCT/US2015/014695.
Andree and Clarke, "Characteristics and Specificity of Phenelzine and Benserazide as Inhibitors of Benzylamine Oxidase and Monoamine Oxidase," *Biochem. Pharmacol.* (1982), 31(5):825-830, Pergamon Press Ltd.
De Girolamo et al., "Protection from MPTP-Induces Neurotoxicity in Differentiating Mouse N2a Neuroblastoma Cells," *J. Neurochem.* (2001), 76:650-660, International Society for Neurochemistry.

A)

c) Proliferation
a) U251S

Figure 5
D)  Viability
a) U251S
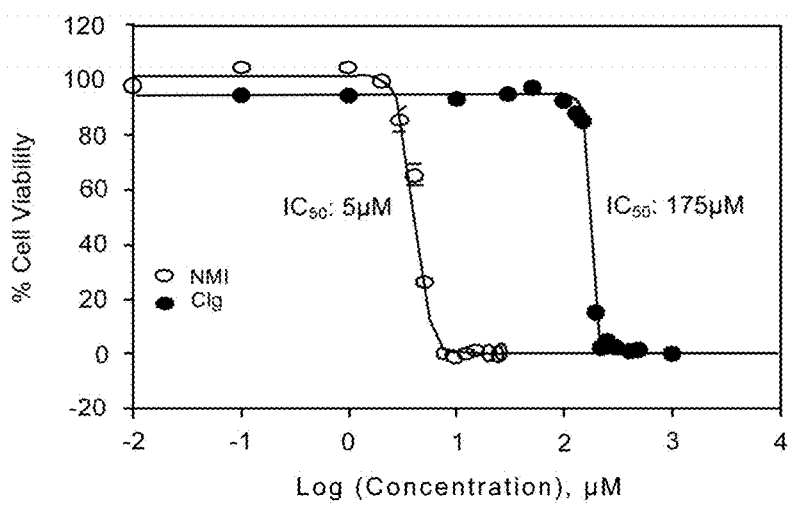
b) U251R
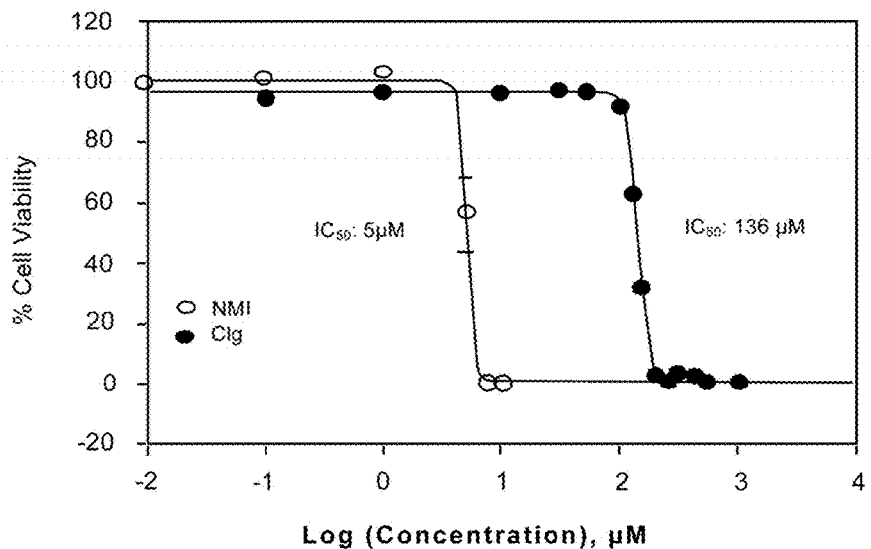

Figure 5
E) Migration
a) U251S
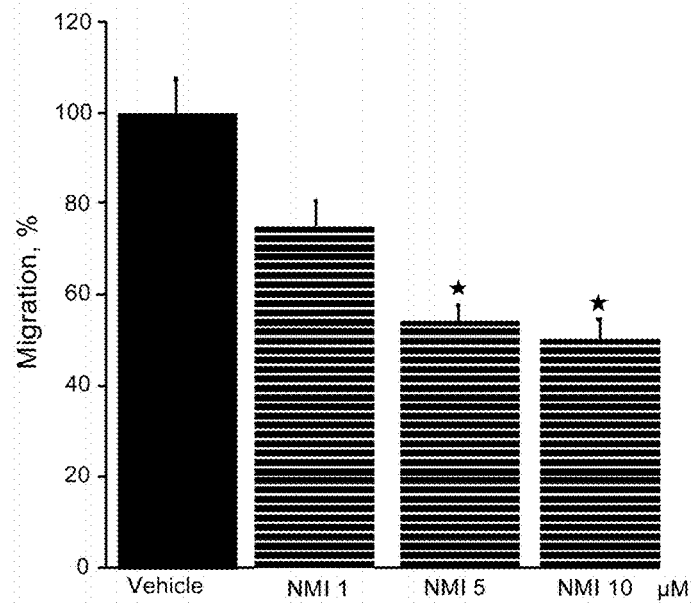
b) U251R
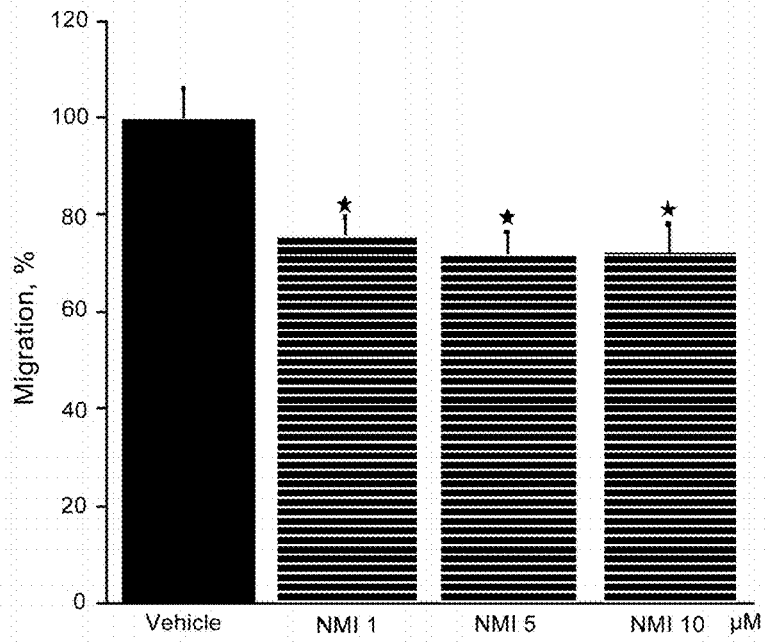

A)

B)

C)

| MAOA activity (nmol/mg/20 min) | | |
|---|---|---|
| | Tumor(GL26) | Surrounding Tissue |
| WT | 17.64 ± 2.71 (n=3) | 16.17 ± 1.01 (n=3) |
| AKO | 6.94 ± 2.34 (n=2) | 0.00 (n=2) |

| Tumor | MAOA activity (nmol/mg/20 min) | % Inhibition | Last day of Survival | p value |
|---|---|---|---|---|
| Vehicle | 24.54 | 100 ± 20.6 | 12 | - |
| Phenelzine (10 mg/Kg) | 2.26 | 87.6 ± 14.2 | 14 | <0.05 |
| Phenelzine +TMZ | 2.63 | 89.2 ± 6.00 | 16 | <0.005 |
| Moclobemide (10 mg/Kg) | 9.15 | 63.7 ± 16.1 | 16 | <0.005 |

Figure 11
MAO A
Normal
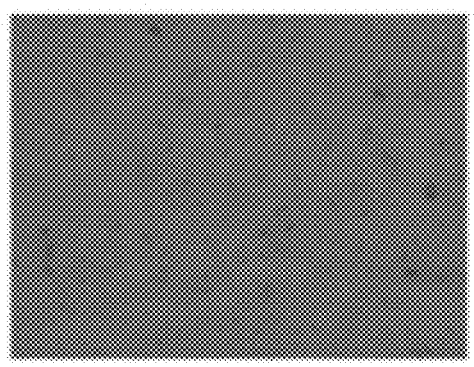
GBM
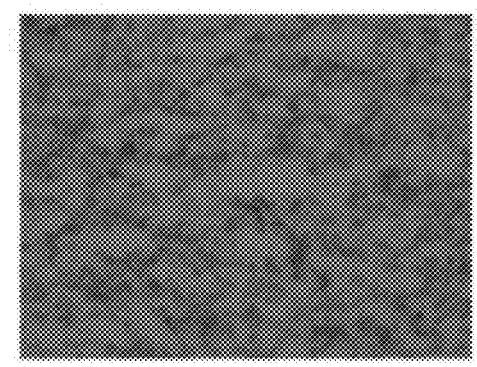
MAO B
Normal
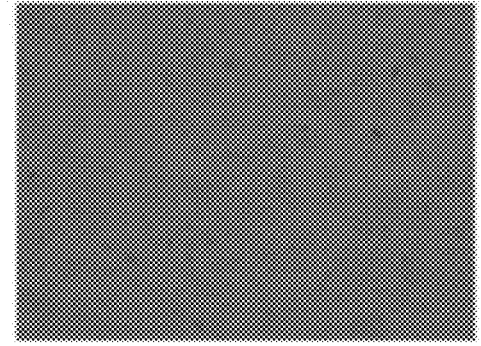
GBM
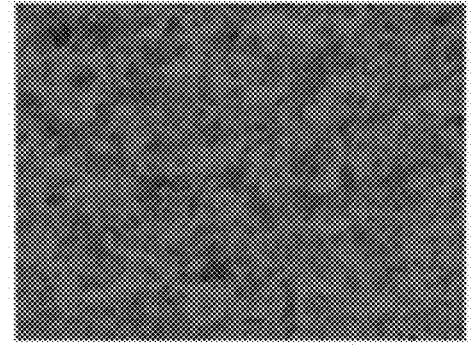

Figure 12

|  |  | MAOA activity(nmol/mg/h) | MAOB activity(nmol/mg/h) |
|---|---|---|---|
| Normal Astrocytes | | 0 | 1.71 |
| Human glioma cells | LN229S | 3.87 | 0.93 |
| | LN229R | 4.35 | 1.08 |
| | U251S | 2.79 | 1.86 |
| | U251R | 0.87 | 1.38 |
| GSC from two patients | USC08 | 6.48 | 1.50 |
| | USC02 | 10.8 | 15.75 |
| Human Brain tissue | Normal | 15.96 | 38.61 |
| | GBM | 18.51 | 77.37 |

| Type of Cancer | | Serotonin as substrate MAO A activity (nmol/mg/20min) |
|---|---|---|
| Prostate | Normal Prostate | No detectable |
| | Human osteotropic postate cancer cells-C4-2B | 78.00 |
| | Androgen-independent Human prostate cancer cell-CW22RV1 | 86.00 |
| | Androgen-dependent Human prostate cancer cell-LNCaP | 130.00 |
| Glioma | Normal Astrocytes | Not detectable |
| | Human 251 TMZ-sensitive glioblastoma multiforme cell-U251S | 0.20 |
| | Human 251 TMZ-insensitive glioblastoma multiforme cell- U251R | 0.31 |
| Pancreas | Normal | No detectable |
| | Human pancreatic cancer *cell*-BxPC-3 | 0.00 |
| | Human pancreatic cancer *cell*-MIA PaPa-2 | 0.00 |
| Lymphoma | Normal | Not determined |
| | U937 | 0.00 |
| | SU-DHL-1 | 0.00 |
| | NU-BL-1 | 0.00 |
| | pre-B acute lymphoblastic leukemia | 0.00 |

Figure 19
A)

|  | MAOA activity (nmol/mg/h) (5HT as substrate) |
|---|---|
| Normal Astrocytes | 0.00 |
| Human Glioma Stem cells USC02 | 10.8 |
| Human Glioma Stem cells USC08 | 6.48 |

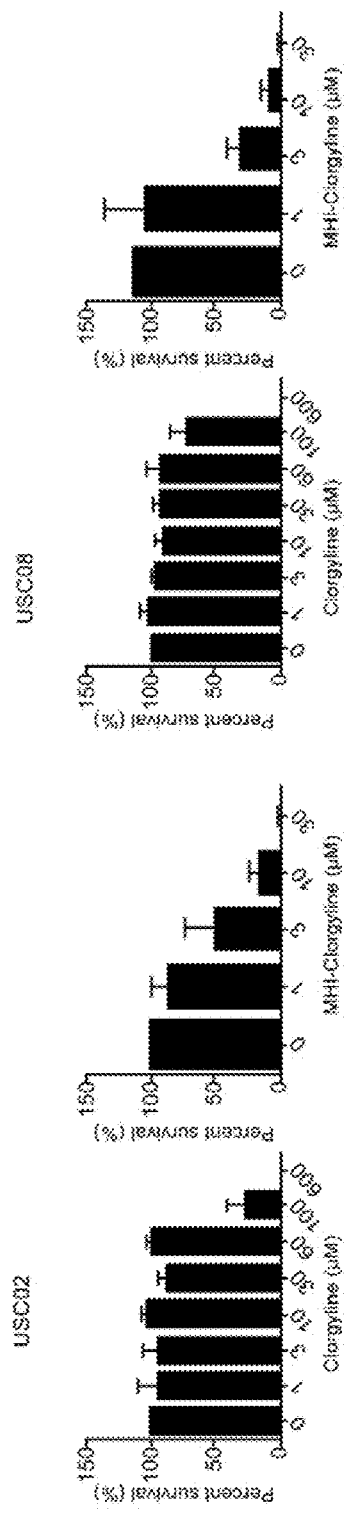

MAO INHIBITORS AND THEIR CONJUGATES AS THERAPEUTICS FOR THE TREATMENT OF BRAIN CANCER

CROSS-REFERENCE TO RELATED APPLICATIONS

This application is a divisional of U.S. application Ser. No. 14/615,416, filed on Feb. 5, 2015, which is a Continuation-in-Part of U.S. application Ser. No. 13/559,431, filed on Jul. 26, 2012, which claims the benefit of priority of U.S. Provisional Application Ser. No. 61/511,920, filed on Jul. 26, 2011, all of which are incorporated herein by reference in their entirety. Also U.S. application Ser. No. 14/615,416 claims the benefit of priority to U.S. Provisional Application Ser. No. 61/937,425, filed on Feb. 7, 2014, the content of which is incorporated herein by reference in its entirety.

STATEMENT REGARDING FEDERALLY SPONSORED RESEARCH AND DEVELOPMENT

This invention was made with government support under Contract No. R01-MH39085 awarded by the National Institute of Health. The government has certain rights in the invention.

FIELD OF THE INVENTION

The present invention relates generally to inhibition of monoamine oxidases (MAOs) and their inhibitors (MAOIs) in the treatment of brain cancer.

BACKGROUND OF THE INVENTION

Glioblastoma multiforme (GBM) is the most malignant form of primary brain tumors, with a median survival time of approximately 14 months (1). Current treatments include surgery, radiation and chemotherapy. The chemotherapeutic agent used for GBM treatment is the DNA alkylating agent, temozolomide (TMZ). This drug is effective in combination with surgery and radiation or as a stand-alone chemotherapy (2). Unfortunately following treatment, tumors usually recur, and no longer respond to TMZ. Therapy options are then very limited. Therefore, the identification of a drug that is well-tolerated, cytotoxic for gliomas and able to cross the blood-brain-barrier would be extremely useful for the treatment of TMZ-resistant recurrent GBM.

Monoamine oxidase A (MAO A) is a mitochondrial-bound enzyme which catalyzes oxidative deamination of monoamine neurotransmitters such as serotonin, norepinephrine, dopamine and produces hydrogen peroxide ($H_2O_2$), a reactive oxygen species (ROS) which predisposes cancer cells to DNA damage, thereby promoting tumor initiation and progression. Previous studies in the inventors' lab showed that knock-down (KD) or pharmacological inhibition of MAO A in prostate cancer reduced or eliminated cancer progression (3). Clorgyline, a selective MAO A inhibitor (MAOI) which crosses the blood-brain-barrier (BBB), is used as an anti-depressant, and causes reduced prostate cancer growth in vivo. The clorgyline conjugate NMI significantly reduced tumor growth, and is selectively cytotoxic for cancer cells in vitro and in vivo, also crosses the BBB, and is visualized by near-infrared imaging useful for cancer diagnosis and monitoring cancer progression.

Increased MAO A expression has previously been reported in several cancers including prostate cancer and renal cell carcinoma (15, 16) and is down regulated in majority of human cancers, based on an ensemble of cancer GeneChip dataset (17). Previously, the inventors showed that elevated expressions of MAO A promoted prostate tumorigenesis, and induced epithelial-to-mesenchymal transition (EMT) in prostate cancer cells. Furthermore, inhibition of MAO A reduced the growth of LNCaP PCa cells in vitro and tumor xenograft in vivo (18, 3)

SUMMARY OF THE INVENTION

One aspect of the present invention is direct to compounds and pharmaceutical compositions useful for the treatment of brain cancer and to treatment methods for treating brain cancer using the compounds and pharmaceutical compositions of the present invention.

A method of treating brain cancer according to the present invention comprises administering to a patient having brain cancer and in need of treatment an effective amount of an MAO inhibitor. The brain cancer to be treated may be a glioblastoma, and can include Glioblastoma multiforme. The brain cancer to be treated may also be TMZ resistant glioblastoma or Glioblastoma multiforme.

The MAO inhibitor is preferably selected from the group consisting of

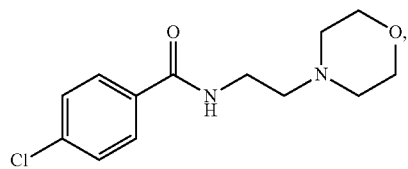

Moclobemide

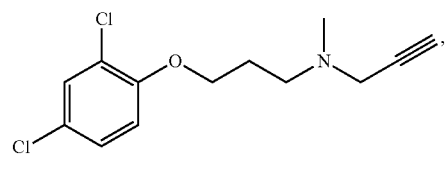

Clorgyline

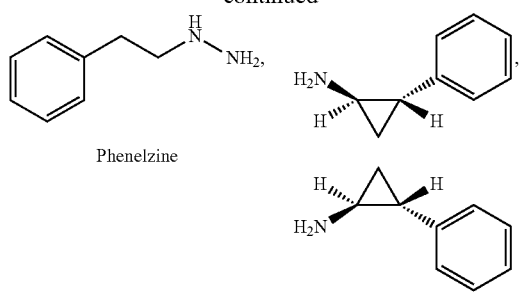

Phenelzine

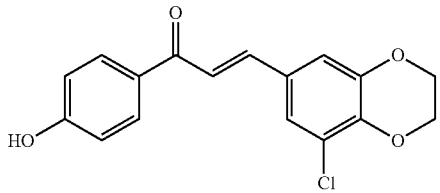

Tranylcypromine enantiomers

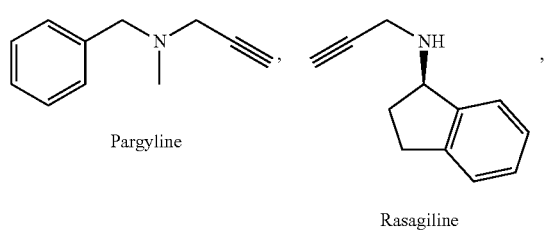

Pargyline , Rasagiline

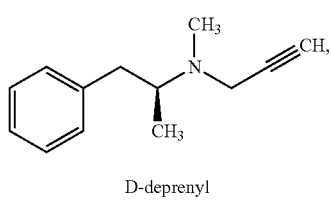

D-deprenyl

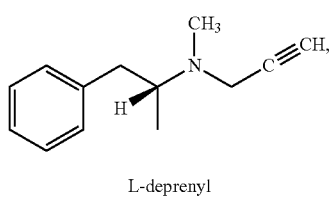

L-deprenyl

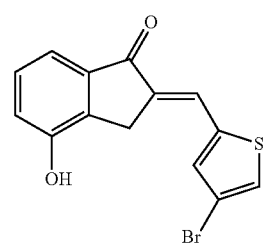

11

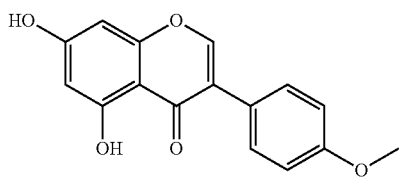

12

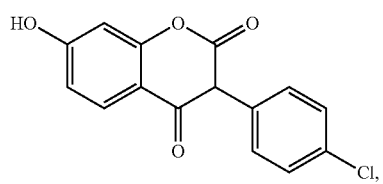

13

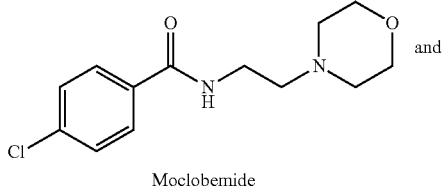

14

Preferably, the MAO inhibitor is selected from the group consisting of

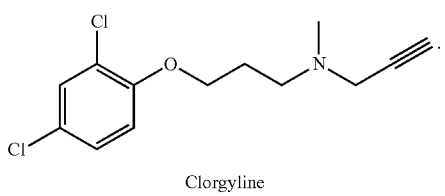

Moclobemide and

Clorgyline

In a preferred embodiment, the MOA inhibitor may be covalently linked to a near infrared dye via a linker. The near infrared dye comprises a polyene functional groups, and is preferably a near infrared dye is selected from the group consisting of IR-783, IR-780, IR-786 and MHI-148, and more preferably, MHI-148.

In a preferred embodiment, the MAO inhibitor is selected from the group consisting of a conjugate of MHI-148 and moclobemide (MHI-moclobemide), a conjugate of MHI-148 and phenelzine, a conjugate of MHI-148 and tranylcypromine, a conjugate of MHI-148 and pargyline, a conjugate of MHI-148 and clorgyline.

Preferred examples include:
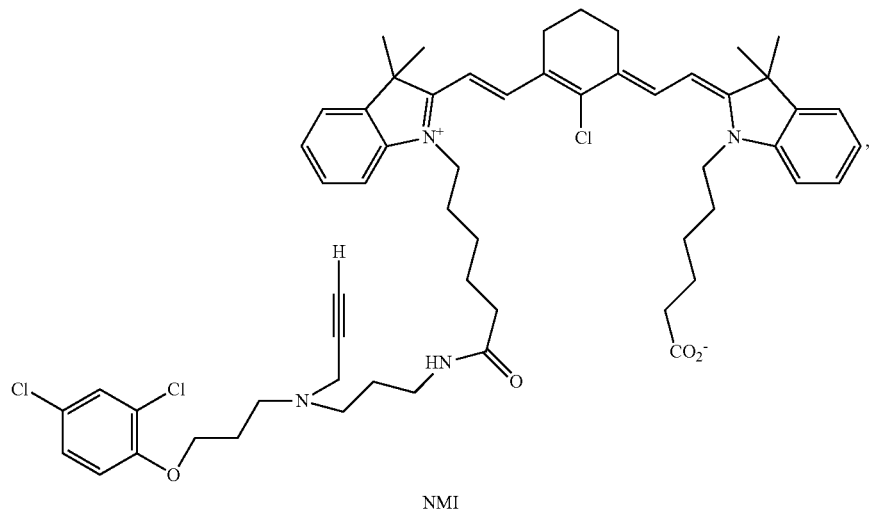
NMI
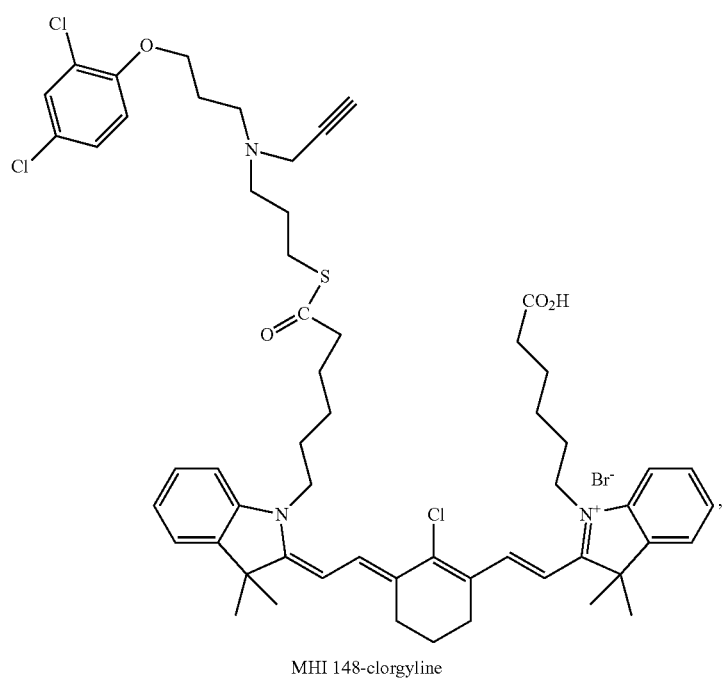
MHI 148-clorgyline
and salts, carboxylic acids or esters thereof.

Other examples include compounds having the formula:

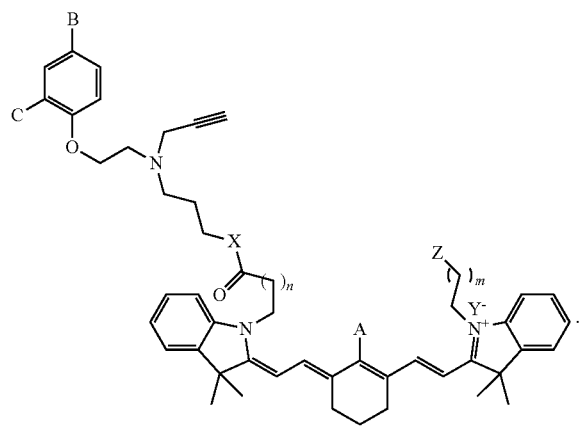

A, B, or C = F, Cl, Br, I
X = NH, O, S
Y = Cl, Br, I, mesyl, tosyl
m, n = 1-15

Another embodiment of the present invention is a compound comprising a salt of

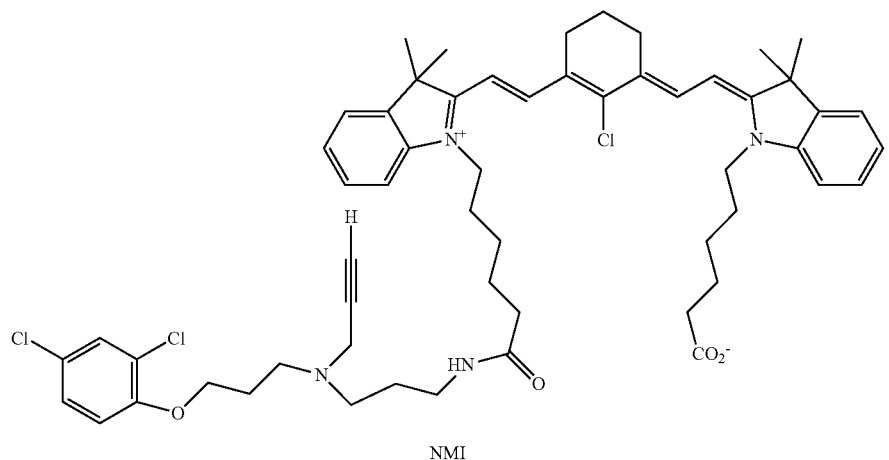

NMI or a carboxylic acid or ester analog thereof, and to pharmaceutical compositions comprised thereof and to methods and uses thereof for treating brain cancer.

In another embodiment, the present invention is directed to compounds and pharmaceutical compositions useful for the treatment of drug resistant brain cancer and to treatment methods for the treatment of drug resistant brain cancer. The methods of treating drug resistant brain cancer according to the present invention generally include administering to patient in need thereof an effective amount of a MAO inhibitor.

In another embodiment, the present invention is directed to compounds and pharmaceutical compositions useful for sensitizing TMZ resistant brain cancer to TMZ and to treatment methods for the treatment of TMZ resistant brain cancer. The methods of treating drug sensitizing TMZ resistant brain cancer to TMZ treatment according to the present invention generally include administering to patient in need thereof an effective amount of a MAO inhibitor. The method preferably includes concurrently or sequentially administering an effective amount of TMZ.

The present invention shows that inhibition of monoamine oxidase A (MAO A) reduces tumor growth and increases survival of temozolomide (TMZ)-resistant gliomas. Gliomas initially respond to TMZ; but patients usually become resistant to this drug and tumors recur. No treatment is then available. MAO A is a mitochondrial enzyme which oxidatively deaminates monoamine neurotransmitters, produces hydrogen peroxide causing cell damage and cancer. Human gliomas express MAO A, whereas normal astrocytes have no detectable MAO A activity. In vitro studies showed that both MAO inhibitor clorgyline and NMI, defined herein, increased TMZ sensitivity in drug-sensitive glioma cells, while in TMZ-resistant cells only NMI sensitized cells but not clorgyline. NMI ($IC_{50}$: 5 μM) is more effective than clorgyline ($IC_{50}$: 140 and 136 μM) for reducing migration in both resistant and sensitive human glioma cells. Mouse GL26 tumor implanted in MAO A KO mice exhibited increased survival compared to wild type, suggesting that MAO A in the microenvironment affects tumor growth and survival. Drug efficacy studies in orthotopic xenograft models showed that both clorgyline and NMI decreased the growth of TMZ-resistant tumors and increase survival (28%, 46%, respectively). Analysis of tumor tissues showed that MAO A inhibitors reduced proliferation, microvessel density, and matrix metalloproteases, and increased macrophages infiltration. In summary, the present invention has discovered an important role for MAO A in progression of drug-sensitive and resistant gliomas, and identified MAO A inhibitors and their conjugates as important therapeutic agents for treating drug-resistant brain tumors. The invention shows that MAO A inhibitors are active in vitro and in vivo to reduce tumor progression and prolong survival of patients with drug-resistant gliomas.

BRIEF DESCRIPTION OF THE DRAWINGS

The file of this patent contains at least one drawing executed in color. Copies of this patent with color drawings will be provided by the Office upon request and payment of the necessary fee.

FIG. 11 shows that MAOA expression increased in glioblastoma (GBM) tissue compared to normal brain. Frozen sections of normal and glioma (GBM) brain specimens were stained with anti-MAOA antibody. Positive cells show red precipitate; hematoxylin stains (blue) nucleus. MAOA expression increased in glioblastoma (GBM) tissue compared to normal brain.

FIG. 12 shows that MAO A and MAO B activity in tumor-derived cell lines (LN229, U251), GSC (USC02, USC08) and in GBM but not in normal astrocytes suggests that MAOA activity is associated with cancer progression. Total protein from cells was collected and incubated with 10 μM of $^{14}$C-labeled serotonin at 37° C. for 20 min. Radioactivity was measured by liquid scintillation spectrophotometry.

Figure 1:
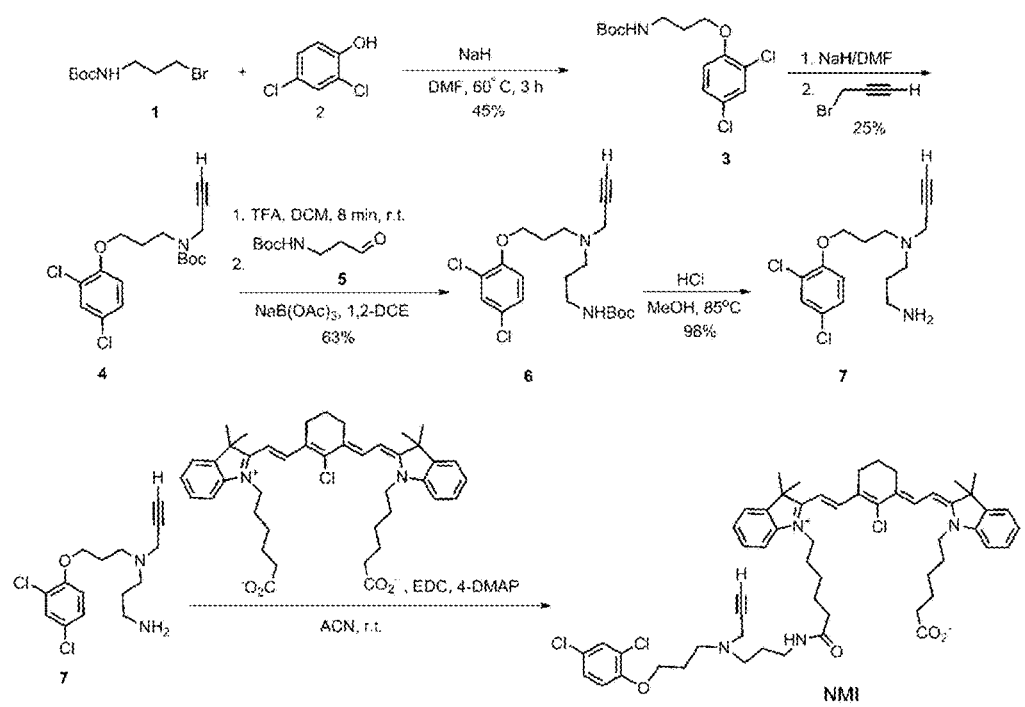
FIG. 1 shows the synthesis of NMI.

FIG. 18. Prostate cancer and glioma have MAO A activity and can be treated with MAO I and MHI-clorgyline. Pancreatic cancer and lymphoma do not have MAO A activity, thus cannot be treated by clorgyline and MHI-clorgyline.

FIG. 19. A) Presence of MAO A activity in gliomas stem cells (GSC) and B) treatment with the clorgyline and MHI-clorgyline, induces glioma stem cell cytotoxicity. (A) GSC, USC08 and USC02, showed MAOA activity. MAOA activity was determined by a radioactivity assay. Cell homogenate were incubated with 10 µM of $^{14}$C-labeled serotonin at 37° C. for 20 min. The product of MAOA catalyzed reaction, 5-HIAA, was extracted and the radioactivity was determined by liquid scintillation spectrophotometry. B) USC08 and USC02 stem cells were treated with Clorgyline and MHI-clorgyline with increasing concentration and sphere formation was measured. Clorgyline and MHI-clorgyline induce the stem cell cytotoxicity.

DETAILED DESCRIPTION OF THE INVENTION

Pharmaceutical compositions suitable use in connection with the present invention are generally prepared by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration should generally be sterile. This is readily accomplished by filtration through sterile filtration membranes, prior to or following lyophilization and reconstitution.

DEFINITIONS

Patients who may benefit from or are in need to the treatment methods of the present invention are those who have been diagnosed with brain cancer.

As used herein, the phrase "treating brain cancer" may include having at least one of the following effects: to inhibit the inhibit the formation or spread of primary tumors, macrometastases or micrometastases, decrease the size of macrometastases or to ameliorate or alleviate one or more symptoms of the disease caused by the brain cancer. An "effective amount" of the pharmaceutical compositions of the present invention is an amount sufficient to carry out a specifically stated purpose. An "effective amount" may be determined empirically and in a routine manners in relation to the stated purpose. Inhibiting or reducing the formation, size or spread of macrometastases or micrometastases may be shown by comparing to untreated controls.

Disclosed herein are results showing that MAO A mediates glioma progression, and inhibiting MAO A activity can decrease glioma growth, thereby increasing survival. The data presented here demonstrated that the MAO inhibitors moclobemide, clorgyline and its derivative NMI are active in decreasing tumor growth. It was demonstrated that tissue specimens from GBM patients overexpress MAO A as compared to non-tumor brain tissues. The effects of MAO A inhibitors, currently in use as anti-depressants were examined for the treatment of brain cancer, including drug-resistant gliomas.

The results presented herein demonstrate MAO A's role in brain tumor growth, and tumor microenvironment. One big challenge in the treatment of gliomas is tumor recurrence, and these recurrent tumors are commonly TMZ-resistant. One important aspect of the present invention is that MAO A inhibitors and their conjugates reduce glioma growth and progression in TMZ-resistant, a result of significant clinical significance.

One aspect of the present invention is directed to a compound and pharmaceutical composition used for treating brain cancer, including malignant gliomas, and including Glioblastoma multiforme (GBM). Another aspect is directed to methods of treating the malignant glioma (such as GBM) using the compositions. Compositions in accordance with this aspect of the invention will generally include an MAO inhibitor (i.e. an active agent capable of inhibiting MAO activity); and a physiologically suitable carrier. In one aspect, a method for treating a malignant glioma comprises contacting the glioma with an effective amount of the MAO inhibitor. The method of treating a patient with a malignant glioma or GBM in connection with this aspect of the present invention comprises administering to a patient in need thereof an effective amount of the MAO inhibitor. The MAO inhibitor may be a nano-conjugate with a NIR dye conjugated to a MAO inhibitor.

A second aspect of the present invention is directed to a pharmaceutical composition useful for to reduce GBM progression, and methods of slowing the progression of GBM using the compositions. Slowing the progression, as used herein, includes halting the progression, slowing the progression, or slowing the rate of increase of progression of at least one characteristic of GBM tumors. Compositions in accordance with this aspect of the invention will generally include an MAO inhibitor (i.e. an active agent capable of inhibiting MAO activity); and a physiologically suitable carrier. The method of reducing GBM progression in connection with this aspect of the present invention comprises administering to a patient in need thereof an effective amount of the MAO inhibitor. The MAO inhibitor may be a nano-conjugate with a NIR dye conjugated to a MAO inhibitor.

A third aspect of the present invention is directed to a pharmaceutical composition useful for decreasing GBM cell migration and invasion, and methods of decreasing GBM cell migration and invasion the compositions. Compositions in accordance with this aspect of the invention will generally include an MAO inhibitor (i.e. an active agent capable of inhibiting MAO activity); and a physiologically suitable carrier. The method of decreasing GBM cell migration and invasion in connection with this aspect of the present invention comprises administering to a patient in need thereof an effective amount of the MAO inhibitor. The MAO inhibitor may be a nano-conjugate with a NIR dye conjugated to a MAO inhibitor.

A fourth aspect of the present invention is directed to a pharmaceutical composition useful for decreasing glioma stem cell activity, and methods of decreasing glioma stem cell activity using the compositions. Compositions in accordance with this aspect of the invention will generally include an MAO inhibitor (i.e. an active agent capable of inhibiting MAO activity); and a physiologically suitable carrier. The method of decreasing glioma stem cell activity in connection with this aspect of the present invention comprises administering to a patient in need thereof an effective amount of the MAO inhibitor. The MAO inhibitor may be a nano-conjugate with a NIR dye conjugated to a MAO inhibitor.

A fifth aspect of the present invention is directed to a pharmaceutical composition useful for sensitizing TMZ-resistant gliomas, including TMZ resistant GBM, to TMZ, thereby making these TMZ-resistant cells sensitive to this drug, and methods of sensitizing TMZ-resistant resistant gliomas, including TMA resistant GBM, using the compositions. Compositions in accordance with this aspect of the invention will generally include an MAO inhibitor (i.e. an active agent capable of inhibiting MAO activity); and a physiologically suitable carrier. The method of sensitizing TMZ-resistant GBM to TMZ in connection with this aspect of the present invention comprises administering to a patient in need thereof an effective amount of the MAO inhibitor, sensitizing TMZ-resistant GBM to TMZ, thereby making these TMZ-resistant whereby the amount is effective to sensitive the TMA-resistant GBM cells to TMZ. The MAO inhibitor may be a conjugate with a NIR dye conjugated to a MAO inhibitor.

A sixth aspect of the present invention of the present invention is a combination treatment for the treatment of malignant gliomas, including GBM, comprising the administration of a combination of TMZ and an MAO inhibitor. TMZ and the MAO inhibitor may be administered concurrently. Conversely, the MAO inhibitor and TMZ may be administered sequentially, with the MAO inhibitor preferably administered first.

Suitable MAO inhibitors, including suitable nano-conjugates thereof, include those described in U.S. patent application Ser. No. 13/353,094 filed Jul. 26, 2013, which is incorporated herein by references in its entirety. Suitable MAO inhibitor, and nano-conjugates thereof, may be synthesized according to the methods described in U.S. patent application Ser. No. 13/353,094.

In one embodiment, the MAO inhibitor used in connection with the present invention is known in the art. Exemplary MAO inhibitor may include, but not limited to moclobemide, phenelzine, tranylcypromine, pargyline, and clorgyline. Nucleic acids capable of inhibiting, down-regulating or silencing the expression of MAO may also be advantageously used. Exemplary nucleic acid MAO inhibitors may include siRNA, shRNA, antisense, or any other type of nucleic acid-based gene silencing agents commonly known in the art, such as decoys, ribozymes, and aptamers. Such preferred embodiments can be used, either alone or in combination with the described herein pharmaceutical compositions as cancer therapeutics.

Suitable MAO inhibitors include:

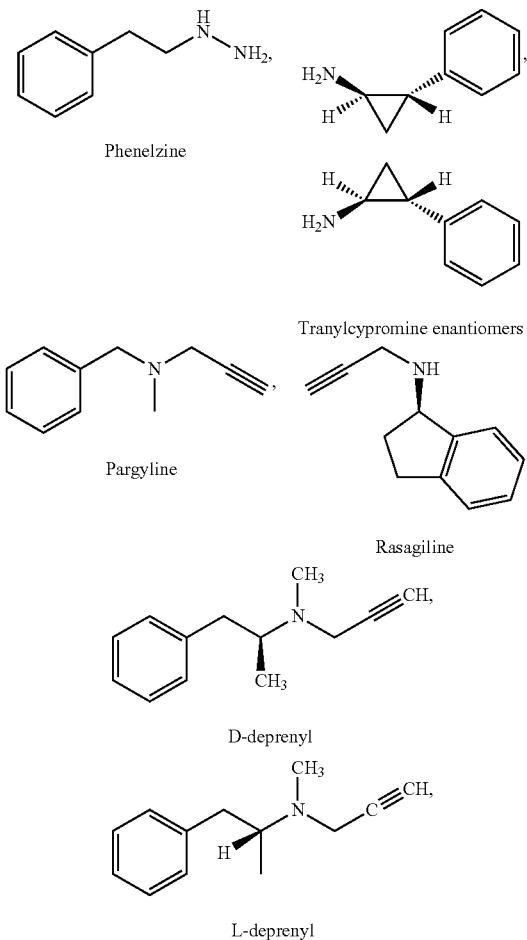

Phenelzine

Tranylcypromine enantiomers

Pargyline

Rasagiline

D-deprenyl

L-deprenyl and compounds 11-14 as shown below:

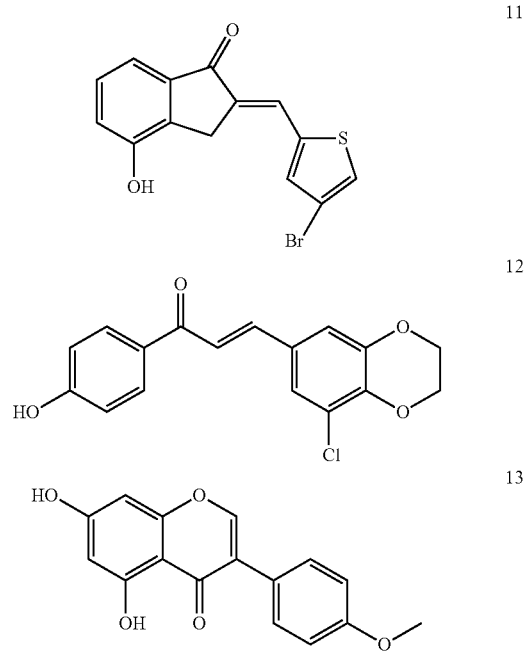

14

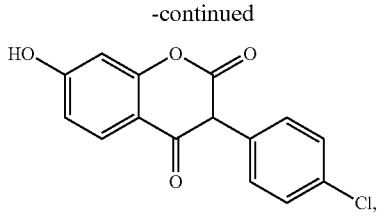

and salts thereof.

As set forth in U.S. patent application Ser. No. 13/353,094 filed Jul. 26, 2013, the MAO inhibitors may linked to a near IR dye (NIR) to form a conjugate capable of, for instance, preferentially or selectively targeting cancer cells. Conjugates in accordance with this aspect of the invention will generally have an NIR dye nanoparticle conjugated to an MAO inhibitor. Exemplary NIR dyes may include conjugated polyene functional groups, such as one found in IR-783, IR-780, IR-786, and MHI-148 but are not limited thereto. Exemplary MAO inhibitors include Phenelzine, Tranylcypromine enantiomers, Pargyline, Rasagiline, D-deprenyl, L-deprenyl, and compounds 11-14 as shown below:

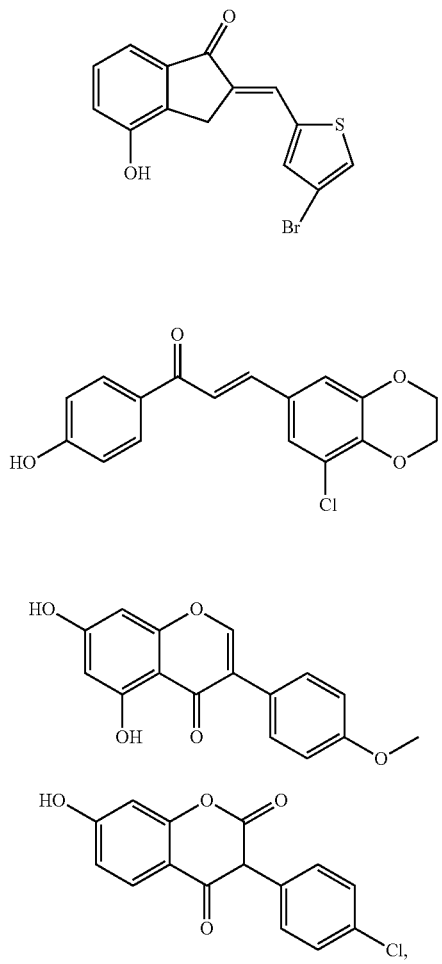

and salts thereof.

Conjugation of the NIR dye to the MAO inhibitor may be achieved by any suitable chemical means known in the art.

In one preferred embodiment, exemplary conjugates of the present invention will generally have at least two functional groups: an MAO inhibitor attached to a light emissive element (e.g. NIR dye nanoparticle) via a linker containing at least one C and two H atoms. Preferably, at least two unsaturated structures containing one unsaturated double or triple bond are linked via a backbone chain of 1-3, 1-5, or 1-15 atoms to one heterocycle.

An exemplary linker is one having the following general formula:

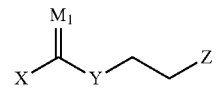

wherein $M_1$ is O or S; and wherein at least two of X, Y, and Z participate in bonds to unsaturated and/or aromatic groups A and B (not shown) which proceed through additional carbon, oxygen or nitrogen atoms. Any of X, Y, and Z not participating in a bond to group A or B is substituted with hydrogen or lower aliphatic group, such as $C_1$-$C_6$ alkyl.

For example, a conjugate in accordance with embodiments of the invention may be one having the following formula:

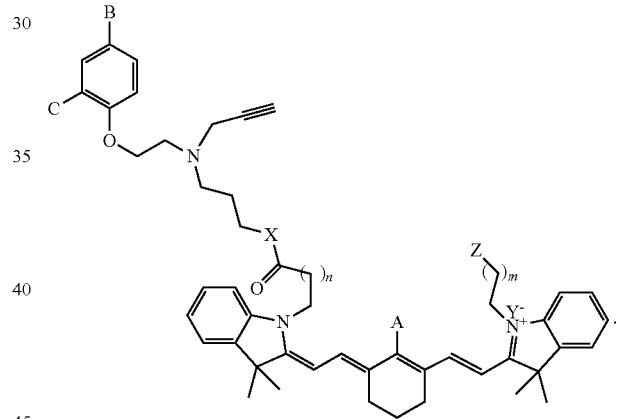

A, B, or C = F, Cl, Br, I
X = NH, O, S
Y = Cl, Br, I, mesyl, tosyl
m, n = 1-15

In another embodiment, X and Y are as above and Z is selected from the group consisting of

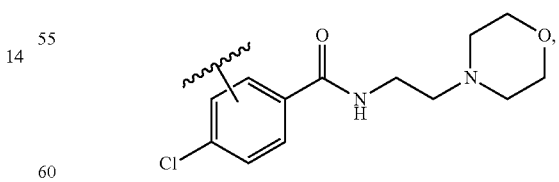

wherein the covalent link is attached to the aromatic ring.

This compound is herein referred to as MHI-moclobemide, a MAO-A specific reversible inhibitor.

In another embodiment, X and Y are same as above, and Z is

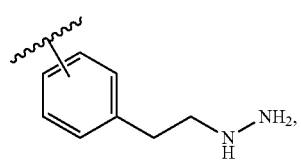

wherein the covalent bond is also attached to the aromatic ring. This compound is herein referred to as MHI-phenelzine, a MAO-A and -B inhibitor.

In still another embodiment, X and Y are same as above, and Z is (±)-trans-2-phenylcyclopropan-1-amine having the formula:

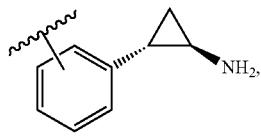

wherein covalent attachment is through the aromatic ring. This compound is herein referred to as MHI-tranylcypromine, which is a MAO-A and -B inhibitor.

In still another embodiment, X and Y are same as above, and Z is N-Benzyl-N-methylprop-2-yn-1-amine, having the following formula:

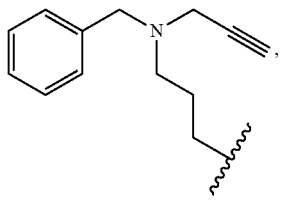 [SMILES: *CCCN(CC#C)Cc1ccccc1]

wherein covalent linkage is attached to the nitrogen as indicated by the curly line. This compound is herein referred to as MHI-pargyline, a MAO-A and -B inhibitor with a preference for MAO-B.

In a preferred embodiment, Y is S; X is a group having the following formula:

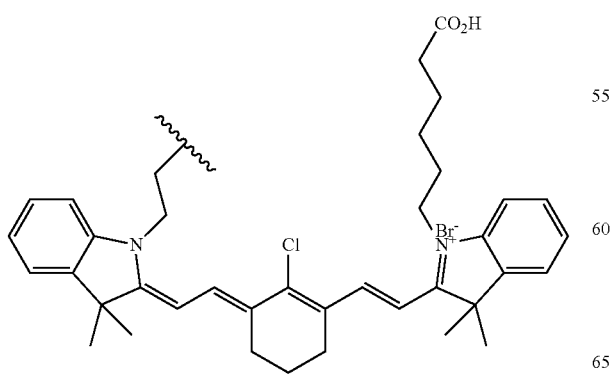

and Z is a group having the following formula:

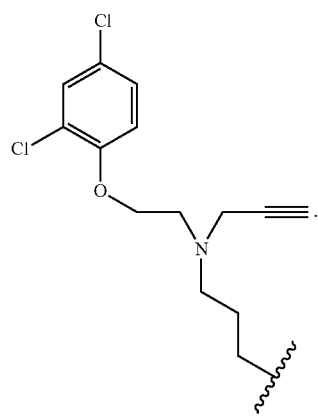 [SMILES: *CCCN(CC#C)CCOc1ccc(Cl)cc1Cl]

This compound is referred to herein as MHI-clorgyline, which is a MAO-A specific irreversible inhibitor.

In yet another embodiment, X and Y are same as above, Z is one selected from the following:

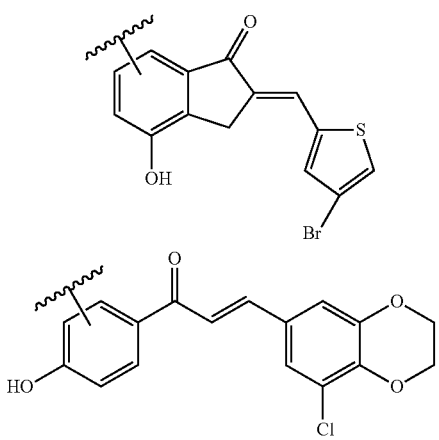

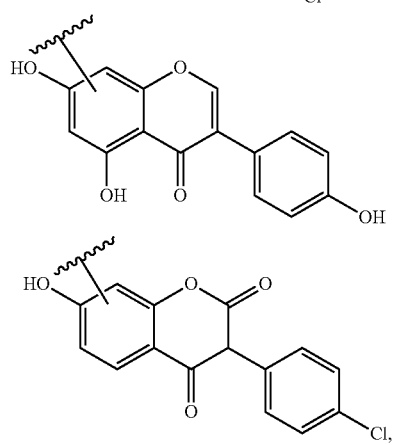

wherein covalent linkage is attached to the aromatic rings. This group of compounds is collectively referred to herein as MHI-MAOIs.

In another embodiment, an MAO inhibitor NIR dye conjugate has the formula:

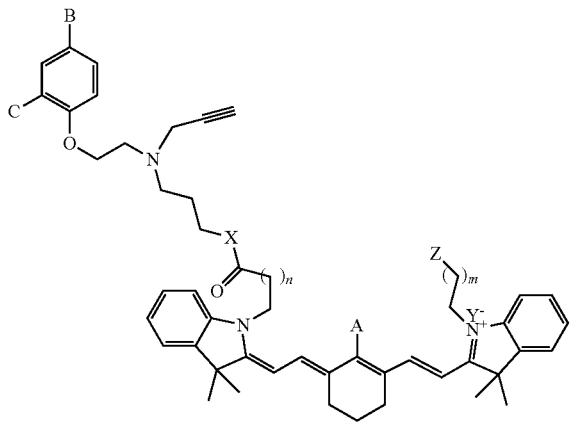

A, B, or C = F, Cl, Br, I
X = NH, O, S
Y = Cl, Br, I, mesyl, tosyl
m, n = 1-15

In one preferred embodiment and to improve the targeting of MAO inhibitors specifically to tumors, the inventors designed an exemplary NIR dye-MAOA inhibitor conjugate, NMI, evidencing that NIR dye-MAOA conjugates specifically target the mitochondria of cancer cells without affecting normal cells (19). NMI is shown in an anionic form as follows:

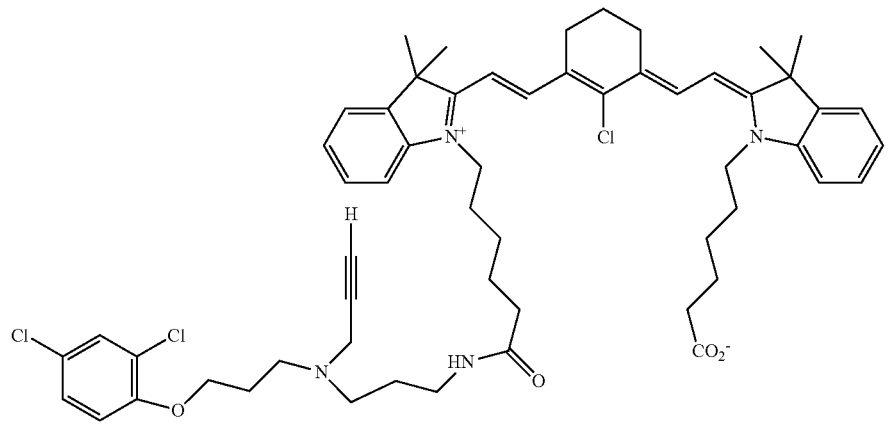

As used herein, NMI includes salt forms of the anion or the carboxylic acid an ester analog of the salt.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of compounds, for example in their purification by recrystallization. All of these salts may be prepared by conventional means from the corresponding compound by reacting, for example, the appropriate acid or base with the compound. The term "pharmaceutically acceptable salts" refers to non-toxic inorganic or organic acid and/or base addition salts, see, for example, Lit et al., Salt Selection for Basic Drugs (1986), Int J. Pharm., 33, 201-217, incorporated by reference herein NMI comprises clorgyline, an irreversible MAOA inhibitor, conjugated to the NIR dye MHI-148 by an amide bond via a linker. This bifunctional system has the NIR imaging capability for diagnosis as well therapeutic activity to specifically target cancer.

The inventors have, for example, examined the efficacy of clorgyline and MHI-clorgyline on tumor growth both in vitro and in vivo systems. The inventors have shown that these MAO A inhibitors are cytotoxic for GBM cells and glioma stem cells. The inventors have demonstrated that, in the orthotopic in vivo mouse models, MAO inhibitors reduce brain tumor progression of TMZ¬resistant GBM. Furthermore, MAO inhibition affects both the glioma cells and the microenvironment of the tumor.

As shown herein, NMI is targeted specifically to mitochondria in human glioma cell and inhibited MAOA activity. NMI has better efficacy than clorgyline in both in vitro and in vivo assays. NMI inhibited colony formation for drug-sensitive and drug-resistant glioma, and further sensitized the sensitive and resistant glioma cells to TMZ treatment. This indicates that the mechanism(s) by which MAO inhibitors affect glioma cells are independent of TMZ-mediated activity.

These results demonstrate that NMI is 30 times more effective in inducing cytotoxicity in glioma cells as compared to clorgyline, suggesting that this increase in cell death may be the result, at least in part, of the higher accumulation of the NIR conjugate in the cancer cells. The inventors also explored the ability of clorgyline and NMI to affect tumor cell migration a critical characteristic of recurrent glioma and found that NMI significantly inhibited the migration of human glioma cells, however clorgyline did not show any significant efficacy. This observation is also consistent with the concept that NMI is effective in depositing high doses of the MAO inhibitor in the tumor cells, and that decreasing MAO A correlates with decreased tumor growth. Thus targeting the tumor with the NIR moiety to produce NMI is a far more effective inhibitor of tumor growth.

Cancer cells are usually under persistent pressure of a complex tumor microenvironment, which includes hypoxia, acidosis, oxidative stress and several other factors (21, 22). High oxidative stress results in elevated expression of reactive oxygen species (ROS) such as, hydrogen peroxide (23). MAOA, when catalyzing oxidative reactions produces hydrogen peroxide as a by-product that can be further converted into other species of ROS (24). The inventors' results showed reduced tumor growth and increased survival in MAO A KO mice as compared to wildtype. Interestingly, it was found that MAO A activity in the tumor and surrounding tissue was lower compared to wildtype, suggesting that MAO A in the microenvironment may affect glioma growth and survival. Inspired by these results the inventors explored the potential of other MAO inhibitors on tumor growth. The intracranial xenograft in vivo mouse model demonstrated increased survival response with moclobemide and in combination with phenelzine and TMZ. These data showed that a variety of MAO inhibitors were effective in decreasing tumor growth. The in vivo studies using intracranial xenograft mouse models showed that clorgyline (10 mg/kg) and NMI (5 mg/kg) both reduced the rate of tumor growth and increased survival. The results also showed that the combination of TMZ and clorgyline or NMI exhibited a significant additive effect for survival, compared to each drug alone. NMI (5 mg/kg) showed significant inhibitory efficacy on tumor xenograft growth, and also showed selective localization to the tumor. These data indicated that NMI was more effective than clorgyline alone, and likely to be more useful especially for TMZ-resistant gliomas.

To determine the potential mechanisms of the in vivo effects of MAO A inhibitors, tumor tissues from treated animals were examined for several characteristics including microvessel density. The data indicate that both clorgyline and NMI decrease blood vessel growth. The reasons for this decrease are not clear. Clorgyline and NMI do not appear to affect normal blood vessels, since the blood vessel density in the adjacent brain parenchyma did not appear to exhibit abnormal density or vascular structure. Thus the MAO A inhibitors specifically affect the tumor vasculature. Since the microenvironment of the tumor vasculature often expresses high levels of vascular endothelial growth factor (VEGF), and basic fibroblast growth factor (bFGF), as well as low levels of thrombospondin-1 (TSP-1), compared to normal brain (25, 26), there is the possibility that MAO A inhibitors may also regulate these growth factors.

Tumor tissues from animal treated with MAO inhibitors exhibited high numbers of macrophages, as compared to control tissues. There is considerable evidence that the immune system, especially macrophages, is important in regulating tumor progression (10). Proinflammatory macrophages generally decrease tumor growth, while immune suppressive, anti-inflammatory macrophages maintain or enhance tumor growth (27). A characteristic of proinflammatory macrophages is the production of TNF-α. Our immunohistochemistry staining data showed that NMI-treated tissues demonstrated a significant increase in TNF-α, indicating that the macrophages present here were likely to be proinflammatory cells. Thus MAO inhibitors regulated the activity of macrophages as well as the activity of glioma cells.

In conclusion, the inventors have demonstrated that in vivo MAO A inhibitors reduced glioma growth and increase survival. These effects of MAO inhibitors may be the result of reduced proliferation, increased cytotoxicity, and/or decreased invasion of tumor cells. MAO A inhibitors may also function by regulating macrophage activity and/or decreasing blood vessel density within the tumor. It is likely that MAO A inhibitors performs several different functions, thereby enabling these inhibitors to be effective against drug-resistant gliomas, Thus targeting MAO A for the treatment of glioma is an effective approach to the treatment of recurrent brain tumors.

EXPERIMENTAL

A. Material and Methods

Cell cultures. The human glioma cell line U251 was obtained from American Type Culture Collection; the TMZ-resistant human glioma cells, U251R, was derived as previously described (4). Mouse glioma cell line GL26 was a gift from Dr. Linda Liau, UCLA. All glioma cell lines were cultured in 10% fetal calf serum (FCS) in Dulbecco's Modified Eagle's Media (Life technologies, Carlsbad, Calif.) supplemented with 100 U/mL penicillin and 0.1 mg/mL streptomycin in a humidified incubator at 37° C. and 5% $CO_2$.

MAO A catalytic activity assay. MAOA catalytic activity was determined as described previously (5). Briefly, cell or tissue homogenates were incubated with 1 mM $^{14}C$-5-hydroxytryptamine (5-HT) in assay buffer. Reaction products were extracted and radioactivity was determined by liquid scintillation spectroscopy. For inhibition activity assays, cells were pre-incubated with various compounds at increasing concentrations, for 20 minutes at 37° C. followed by the addition of $^{14}C$ labeled 5-HT at 37° C. for 20 minutes.

Laser-scanning confocal microscopy. Cells were plated in glass bottom microscopy dishes (MatTek) (30,000 cells/400 μl), in standard medium, for 24 hours. Cells were treated with NMI (1 and 5 μM), Mitotracker Green (200 nM) (Life Technologies, Carlsbad, Calif.) and DAPI (1×); and incubated for 3 hours. Imaging was performed on a Zeiss LSM 510 inverted laser-scanning confocal microscope. Excitation wavelengths were set at $\lambda_{max}$=790 nm Chameleon (DAPI, blue excitation), 488 nm (Mitotracker Green, green-yellow excitation) and 633 nm (NMI, red excitation). The data were acquired in a multi-track mode. Images were taken using pinholes of 130-200 μM.

Colony forming assay. Glioma cells were seeded in triplicates, then treated with clorgyline, NMI and TMZ for 48 hours. The medium was then removed and replaced with fresh medium (without drugs). Cells were incubated for an additional 8 to 10 days; colonies were visualized by staining with 1% methylene blue and quantified.

MTS assay. Glioma cells were seeded in quadruplicates, and clorgyline and NMI added for 48 hours. Viability was determined as per manufactures instructions (Promega, Madison, Wis.); and calculated relative to untreated control cells. Data was plotted using SigmaPlot 12.0.

Migration Assay. Cells treated with mitomycin C (10 μg/ml) (Sigma Aldrich, St. Louis, Mo.) for 2 hours; a scratch was made using 200 μL sterile tip. Cells were then treated with drug: and photographed at 0 hours and 20-24 hours. Migration was quantified by measuring the area covered by control versus treated groups using ImageJ.

In vivo studies. All animal protocols were approved by the International Animal Care and Use Committee of USC. Intracranial implantation was performed as previously described (6). For MAOA KO studies (7), C57bl/6 mice were used. $2\times10^4$ luciferase labeled GL-26 mouse glioma cells were implanted intracranially into wild type (WT) (n=4) and MAOA KO (n=4) mice; and imaged on days 6 and 10 post implantation. For treatment studies, tumors cells were implanted and after 6 days treatment were initiated. All compounds were dissolved in 10% DMSO+45% glycerol+45% ethanol and injected subcutaneously; TMZ was given by gavage. Animals were treated daily until death, and survival was recorded.

For the xenograft model, athymic (nu/nu) mice were used. Luciferase-positive ($2 \times 10^5$) TMZ-resistant human glioma cells (U251R) were injected intracranially and imaged after 7 days. Daily (21 days) treatments began after tumors were visible; TMZ was administered for the first 10 days only.

In subcutaneous xenograft studies, $5 \times 10^5$ luciferase-positive cells were injected subcutaneously into athymic mice. Drugs were administered daily for 21 days; and tumor size was monitored. Control animals were treated with vehicle.

Immunohistochemistry (IHC). Frozen tissues were fixed in acetone. IHC was performed as described previously (8). The following primary antibodies were used: F4/80, TGF-β, TNF-α (Abcam, Cambridge, Mass.), Ki67 (Santa Cruz Biotechnology Inc., Santa Cruz, Calif.), CD31 (BD Biosciences, San Jose, Calif.), MMP 9 MAO A (Santa Cruz Biotechnology Inc., Santa Cruz) and biotinylated secondary antibodies (Vector Laboratories, Berlingame, Calif.). Controls included no primary antibody. Images were analyzed using Image J software.

Statistical analysis. All parametric data were analyzed using the two-tailed student t-test to calculate the significance values. A probability value (p) <0.05 was considered statistically significant.

B. Synthesis of NMI

General Synthetic Methods

All reagents and solvents were obtained from commercial sources and were used as received unless otherwise stated. All reactions involving moisture-sensitive reagents were conducted under argon atmosphere with anhydrous solvents and flame-dried glassware. Hygroscopic liquids were transferred via a syringe and were introduced into reaction vessels through rubber septa. Reaction product solutions were concentrated using a rotary evaporator at 30-150 mm Hg. Column chromatography was performed on silica gel (230-400 mesh) using reagent grade solvents. Analytical thin-layer chromatography (TLC) was performed on glass-backed, pre-coated plates (0.25 mm, silica gel 60, F-254, EM Science). Analytical HPLC were performed on Microsorb-MV $C_8$ reverse-phase column (250×4.6 mm, Varian) using Shimadzu LC-10A VP pump and Shimadzu SPD 10A VP UV-vis variable-wavelength detector. Preparative HPLC purifications were carried out with $C_8$ reverse phase preparative column (Grace Davison). The flow rate for preparative reverse-phase HPLC was 4 mL/min. In all cases, 5%-95% gradients of acetonitrile in 0.1% aqueous trifluoroacetic acid (TFA) were used as eluents. Water (18 MΩ) was obtained from a Barnstead water purification system, and all buffers were 0.2 μm filtered. Nuclear magnetic resonance (NMR) spectra were collected on instruments in the indicated solvents. The identity and purity of each intermediate and the final product were confirmed by $^1$H NMR (Varian Mercury 400 MHz) and mass spectrometry (Agilent 6520 time-of-flight system). An overview of the synthesis of NMI is disclosed in FIG. 1.

t-Butyl (3-bromopropyl)carbamate (1)

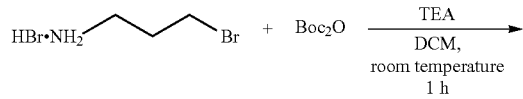

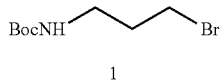

To a 100-mL round-bottom flask equipped with a magnetic stirrer was added 3-bromopropylamine hydrobromide (6.57 g, 30 mmol, 1.0 eq.) and dichloromethane (160 mL). To the resultant solution was added di-tert-butyl dicarbonate (6.54 g, 30 mmol, 1.0 eq.) in dichloromethane (110 mL), followed by triethylamine (4.8 mL, 34.5 mmol, 1.15 eq.). The solution was stirred at room temperature for 95 minutes. The reaction was washed twice with saturated sodium bicarbonate (70 mL, 40 mL) and once with saturated sodium chloride (100 mL). The organic phase was dried over sodium sulfate, filtered, and solvent removed in vacuo to yield 1 (6.91 g, 97% yield). $^1$H NMR (400 MHz, CDCl$_3$) δ: 4.67 (bs, 1 H), 3.43 (t, J=6 Hz, 2H), 3.26 (m, 2 H), 2.04 (m, 2 H), 1.43 (s, 9 H).

t-Butyl 3-(2,4-dichlorophenoxy)propylcarbamate (3)

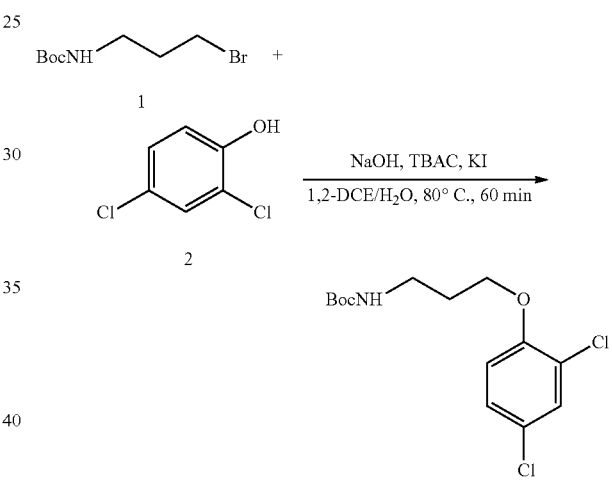

To a 20-mL scintillation vial equipped with a magnetic stirrer was added 2,4-dichlorophenol (2, 237 mg, 1.45 mmol, 1.0 eq.) followed by 1,2-dichloroethane (5 mL). To the resultant solution was added 1 (346 mg, 1.45 mmol, 1.0 eq.), tetrabutylammonium chloride (44.2 mg, 0.159 mmol, 0.11 eq.), followed by potassium iodide (24.1 mg, 0.145 mmol, 1.0 eq). NaOH (5 mL of 10%) was added and the mixture was stirred at 80° C. for 1 h. The biphasic mixture was partitioned and the aqueous layer was extracted twice with DCM (7 mL). The organic phases were pooled, dried over magnesium sulfate, filtered, and then concentrated. The material (512.7 mg) was then columned over silica gel (2.5"×1", height×width) eluting with 100 mL 10% ethyl acetate in hexanes, 100 mL 15% ethyl acetate in hexanes, and 100 mL 25% ethyl acetate. Product 3 elutes in 15% ethyl acetate fractions. Yield 310 mg (67%). $^1$H NMR (400 MHz, CDCl3) δ: 7.32 (d, J=2.4 Hz, 1H), 7.14 (dd, $J_1$=8.8 Hz, $J_2$=2.4, 1 H), 6.80 (d, $J_1$=5.2 Hz, 1 H), 5.18 (bs, 1 H), 4.04 (t, J=6 Hz, 2 H), 3.34 (m, 2 H), 2.00 (m, 2 H), 1.41 (s, 9 H).

t-Butyl 3-(2,4-dichlorophenoxy)propyl(prop-2-ynyl)carbamate (4)

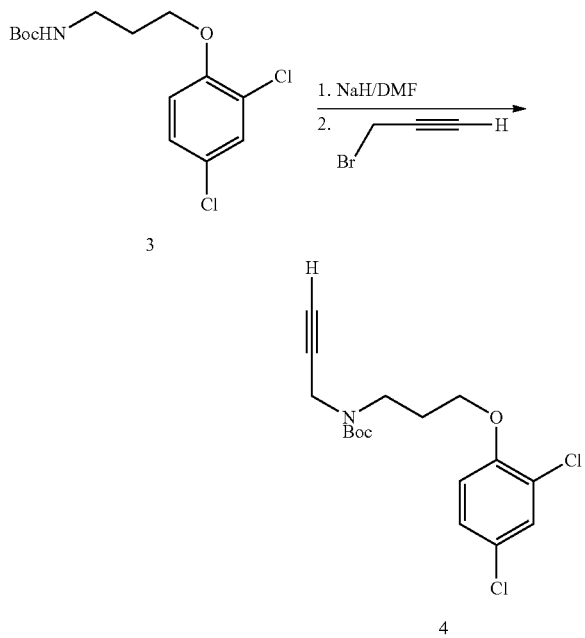

To a 20-mL scintillation vial was added 3 (500 mg, 1.57 mmol, 1.0 eq) followed by sodium hydride (63 mg, 1.57 mmol, 1.0 eq.). The resulting solution was stirred for 15 min with venting to atmosphere, followed by the addition of propargyl bromide (470 μL of 80% solution in toluene (w/v), 3.14 mmol, 2.0 eq.). Note: the solution changes color from yellowish to brown upon addition of propargyl bromide. The reaction was stirred at room temperature for 4 h and solvent was removed via an airstream and the residue was dried in vacuo. The residue was reconstituted in 5 mL DCM and 1.65 g of celite-545 was added. The mixture was then evaporated to dryness. This material was loaded onto a 5"×1" (height× width) plug of SiO$_2$ equilibrated with hexanes and product was eluted with 100 mL 2% ethyl acetate in hexanes, 200 mL 5% ethyl acetate in hexanes, and 200 mL 30% ethyl acetate in hexanes. Fractions containing product were pooled (product elutes between 5% and 30% ethyl acetate in hexanes). Yield 292.6 mg of 4 (52% yield) $^1$H NMR (400 MHz, CDCl3) δ: 7.35 (d, J=2.8 Hz, 1 H), 7.16 (dd, J$_1$=9.2 Hz, J$_2$=2.8, 1 H), 6.82 (d, J$_1$=8.8 Hz, 1 H), 5.18 (bs, 1 H), 4.05 (m, 4 H), 3.55 (t, J=7.2 Hz, 2 H), 2.18 (t, J=2.4 Hz, 2 H), 2.00 (m, 2 H), 1.43 (s, 9 H).

N-(3-(2,4-dichlorophenoxy)propyl)prop-2-yn-1-aminium trifluoroacetate

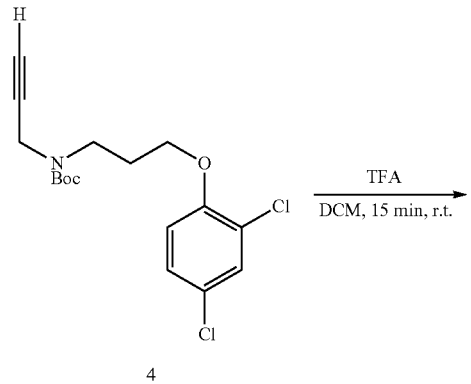

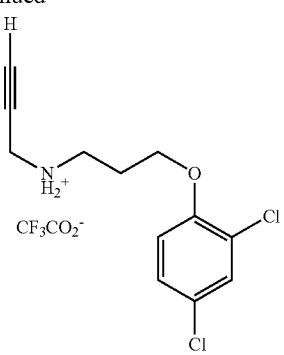

To a solution of tert-butyl 3-(2,4-dichlorophenoxy)propyl (prop-2-ynyl)carbamate 4 (147.6 mg, 412 μmol) in 4 mL DCM in a 20 mL-scintillation vial equipped with a stir bar was added 1 mL TFA at room temperature while stirring. After 15 min, HPLC (5-95% B (A=0.05% aqueous TFA; B=acetonitrile) over 20 min, 0.8 mL/min) indicated completion of the reaction. The solvents were removed under reduced pressure. The residue was co-evaporated with ACN times and then used in the next step without further purification.

t-Butyl (3-oxopropyl)carbamate (5)

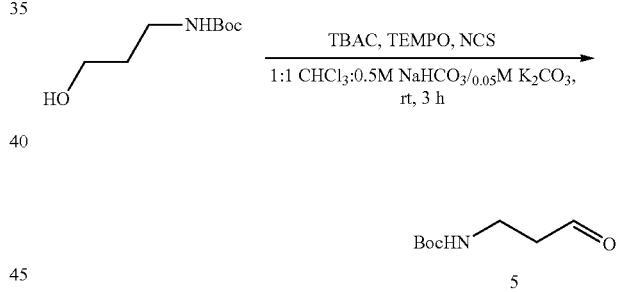

To a 100 mL round bottom flask was added t-butyl (3-hydroxypropyl)carbamate (1.8 g, 10.3 mmol, 1.0 eq.) followed by 35 mL of CHCl$_3$ and 35 mL of 0.5M NaHCO$_3$/0.05M K$_2$CO$_3$. To this mixture was added tetrabutylammonium chloride (288 mg, 1.04 mmol, 0.1 eq.), TEMPO (162 mg, 1.04 mmol, 0.1 eq.), and N-chlorosuccinimide (2.1 g, 15.7 mmol, 1.53 eq.) with vigorous stirring. After three hours the phases were separated, the organic layer was dried, and solvent was removed to give a viscous orange oil. This material was subjected to column chromatography over silica gel using a 4"×1" (height×width) plug of SiO$_2$ and eluting with 75 mL hexanes, 100 mL 20% ethyl acetate in hexanes, 100 mL 30% ethyl acetate in hexanes, 50 mL ethyl acetate. Yield 732.8 mg (41%).

t-Butyl (3-((3-2,4-dichlorophenoxy)propyl)(prop-2-yn-yl)amino)propyl)carbmate (6)

N1-(3-(2,4-dichlorophenoxy)propyl)-N1-(prop-2-yn-1-yl)propane-1,3-diaminium 2,2,2-trifluoroacetate (7)

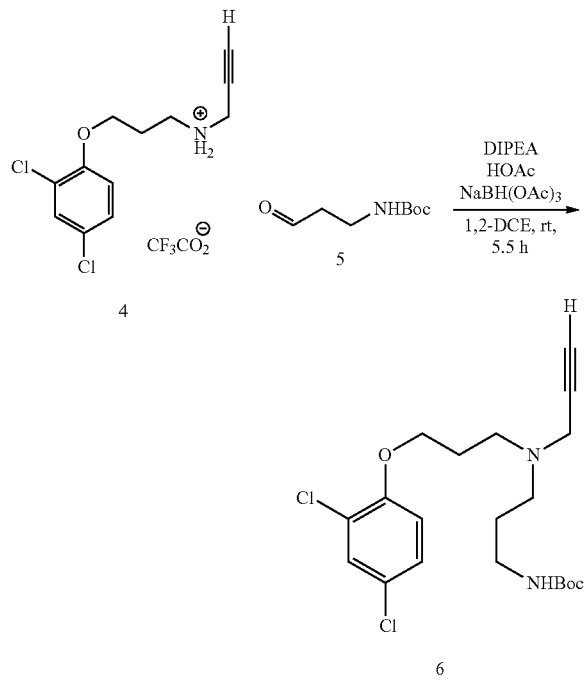

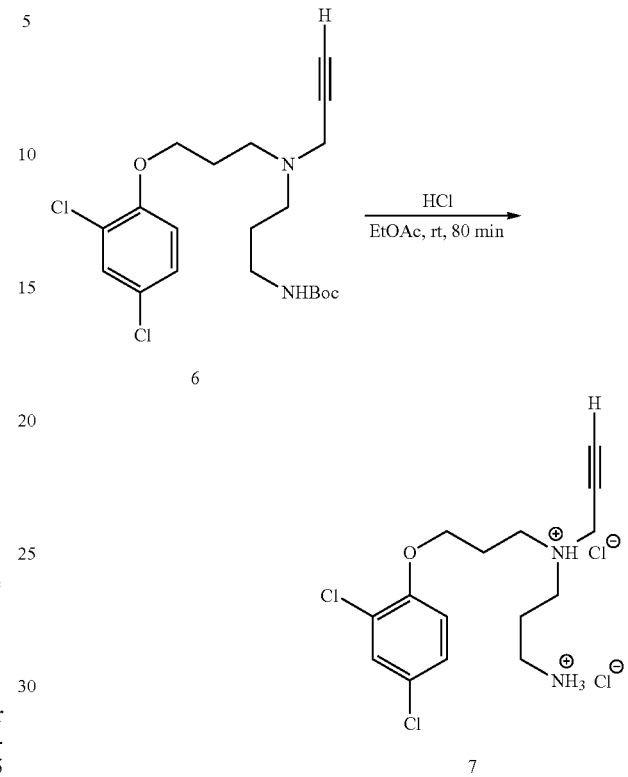

To 100-mL round bottom flask equipped with a stir bar was added N-(3-(2,4-dichlorophenoxy)propyl)prop-2-yn-1-aminium trifluoroacetate 4 (1.25 g, 3.36 mmol, 1.0 eq.) in 25 mL 1,2-DCE. Next, 5 (0.641 mg, 3.4 mmol, 1.1 eq.) was added followed by DIPEA (584 μL, 3.36 mmol, 1.0 eq), acetic acid (330 μL, 5.81 mmol, 1.73 eq.), and sodium triacetoxyborohydride (1.14 g, 5.38 mmol, 1.6 eq.). The reaction was stirred for 5.5 h until approximately 85% conversion was reached, at which point the organic layer was washed twice with sodium bicarbonate (100 mL), dried over anhydrous MgSO₄, filtered, and solvent was removed in vacuo to give 1.12 g of crude 6. This material was used in the next step without further purification.

A solution of N-(3-(2,4-dichlorophenoxy)propyl)-N-(prop-2-yn-1-yl)propane-1,3-diaminium chloride 7 (16 mg, 38.5 μmol) in 10 mL ethyl acetate containing 248 mg of HCl was stirred mechanically. The resulting reaction was stirred at room temperature for 80 min before reaction completion was confirmed by LC/MS. The product was evaporated under reduced pressure and used in the next step without further purification.

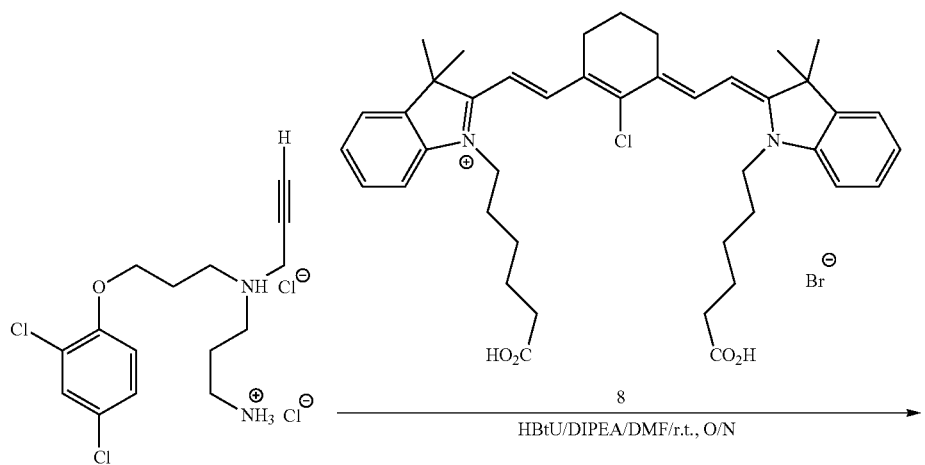

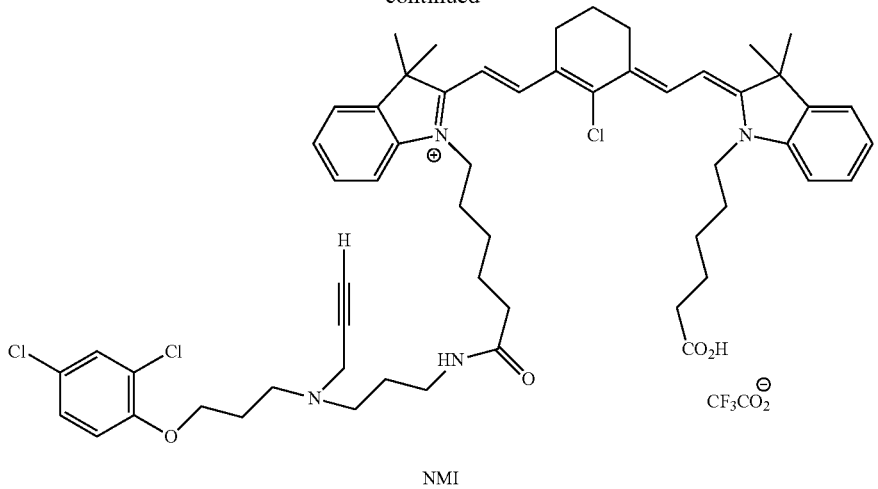

NMI

To a 20-mL scintillation vial was added MHI-148 dye 8 (5.79 mg, 8.47 μmol) followed by DMF (500 μL), DIPEA (1.1 μL, 8.47 μmol, 1.0 eq.), and HBtU (3.2 mg, 8.47 μmol, 1.0 eq.). The mixture was stirred for 10 min at room temperature after which time 7 (4.6 mg, 8.47 μmol, 1.0 eq.) and DIPEA (2.2 μL, 16.94 μmol, 2.0 eq.) in DMF (500 μL) were added. The reaction was covered in foil, and stirred overnight at room temperature. The DMF was evaporated by airstream and the residue was purified on preparative silica gel plates using DCM/isopropanol 1:1 as an eluent. Yield of NMI 1.2 mg (14%). $^1$H NMR (400 MHz, CDCl$_3$): δ 1.49 (m, 2H, γ-C$\underline{H}_2$(COOH)), 1.56 (m, 2H, γ-C$\underline{H}_2$(CONHCH$_2$—)), 1.67 (s, 6H, C$\underline{H}_3$), 1.71 (s, 6H, C$\underline{H}_3$), 1.80 (m, 2H, β-C$\underline{H}_2$), 1.82 (m, 2H, β-C$\underline{H}_2$), 1.86 (m, 2H, δ-C$\underline{H}_2$), 1.88 (m, 2H, δ-C$\underline{H}_2$), 1.94 (s, 2H, O—CH$_2$C$\underline{H}_2$CH$_2$N—), 1.97 (s, 2H, NH—CH$_2$C$\underline{H}_2$CH$_2$N—), 2.09 (s, 2H, CH$_2$), 2.56-2.57 (m, 4H, α-CH$_2$), 2.68-2.70 (m, 4H, C$\underline{H}_2$NC$\underline{H}_2$), 2.71 (s, 2H, CH$_2$C≡), 2.75 (s, 2H, CH$_2$C≡), 3.38 (m, 2H, —NHC$\underline{H}_2$), 4.04 (t, 1H, $\underline{H}$C≡C—), 4.05 (t, 4H, N—C$\underline{H}_2$), 4.05 (t, 2H, O—C$\underline{H}_2$), 4.07 (t, 2H, CH$_2$C≡), 4.57 (bs, 1H, N$\underline{H}$—CH$_2$CH$_2$), 6.04 (d, 1H, C$\underline{H}$=CH), 6.32 (d, 1H, C$\underline{H}$=CH), 6.85 (d, 1H, Ar—$\underline{H}$), 7.05 (d, 1H, Ar—$\underline{H}$), 7.17-7.42 (m, 9H, Ar—$\underline{H}$), 8.28 (d, 1H, CH=C$\underline{H}$), 8.40 (d, 1H, CH=C$\underline{H}$). HRMS calcd. for C$_{57}$H$_{69}$Cl$_3$N$_3$O$_4$SC$_{57}$H$_{70}$Cl$_3$N$_4$O$_4$ m/z 979.4457; observed m/z 979.4463.

Synthesis Of Mhi-148-Clorgline Conjugate

Synthesis of S-3-bromopropyl ethanethioate

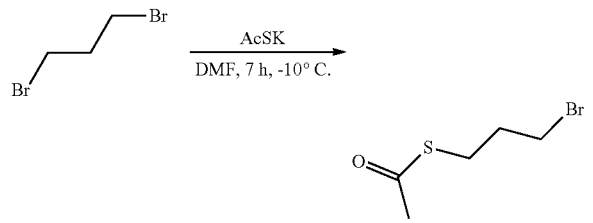

A 250 mL three-neck round-bottom flask equipped with a thermocouple in a glass sleeve, a magnetic stirrer, a vigreux column with an Argon inlet (middle stem) and a sleeved rubber septum stopper was assembled and dried with a heat gun under flow of Ar. Approximately 110-120 mL of anhydrous DMF was added via cannula under Ar. AcSK (11.68 g, 102.3 mmol) was added by portions into the flask while cooled with ice-MeOH bath. The reaction went on for 7 h at about −10° C. The ice-MeOH bath was removed after quenching the reaction by adding 165 mL water. The reaction mixture was partitioned with 300 mL MTBE and 700 mL water. The water layer was washed by 200 mL MTBE. The MTBE layers were washed sequentially with water, saline and NaHCO$_3$, dried by MgSO$_4$, filtered and evaporated. Yield 98.7% (19.1 g).

Synthesis of S-3-((3-(2,4-dichlorophenoxy)propyl)(prop-2-ynyl)amino)propyl ethanethioate

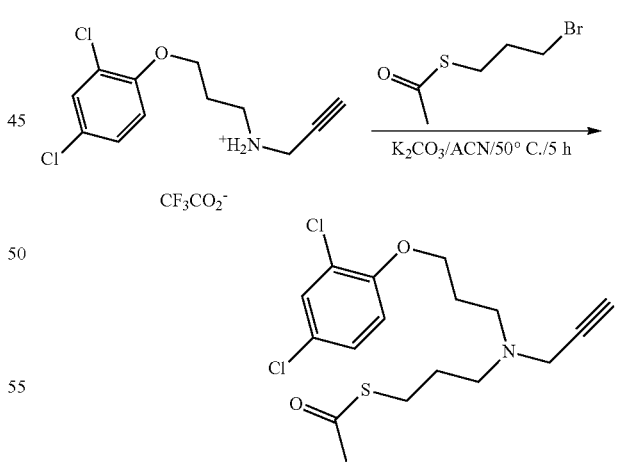

To a solution of N-(3-(2,4-dichlorophenoxy)propyl)prop-2-yn-1-aminium 2,2,2-trifluoroacetate (2.14 mg, 0.05 mmol) in 100 μL ACN in a 5 mL vial equipped with a stir bar, 12.1 mg (0.09 mmol) of K$_2$CO$_3$ and 142.4 mg (0.720 mmol) S-3-bromopropyl ethanethioate was added. The mixture was stirred while heated to 50° C. in an oil bath. TLC was performed (silica gel, MTBE:hexane=9:1 to detect starting material and MTBE:hexane=1:9 to detect the consumption of the thioacetate reagent) to follow the process of the reaction. To a solution of N-(3-(2,4-dichlorophenoxy)propyl)prop-2-yn-1-aminium 2,2,2-trifluoroacetate (17.1 mg, 0.05 mmol) in 800 μL ACN in a 20 mL vial equipped with a stir bar, 120.0 mg (0.870 mmol) of $K_2CO_3$ and 95.2 mg (0.48 mmol) S-3-bromopropyl ethanethioate was added. The mixture was stirred while heated by 50° C. oil bath for 5 h. The reaction mixtures of the two reactions were combined, filtered and evaporated. Crude product (168.4 mg) was obtained and co-evaporated with hexane for 3 times to remove ACN. Silica gel column (1.25 g) was used to purify the crude product. Yield 14% (2.6 mg). Structure of the product was proved by NMR and LC-MS Synthesis of 3-((3-(2,4-dichlorophenoxy)propyl)(prop-2-ynyl)amino)propane-1-thiol

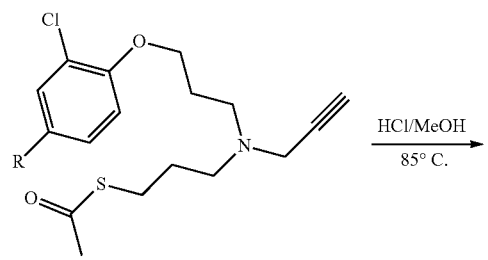

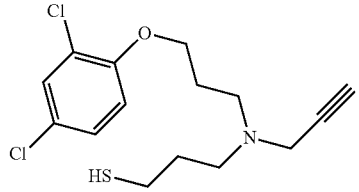

A solution of S-3-((3-(2,4-dichlorophenoxy)propyl)(prop-2-ynyl)amino)propyl ethanethioate (1.17 mg, 3.10 μmol) in 200 μL ACN was added into a 20 mL vial equipped with a stir bar, evaporated and then co-evaporated with MeOH for 3 times to remove ACN. MeOH/HCl (200 μL) was added into the vial and then the vial was heated by 85° C. oil bath for 6 h. The reaction mixture was evaporated, co-evaporated sequentially by MeOH for 3 times and ACN for 3 times, and then used in the next step without further purification.

Synthesis of MHI 148-clorgyline conjugate

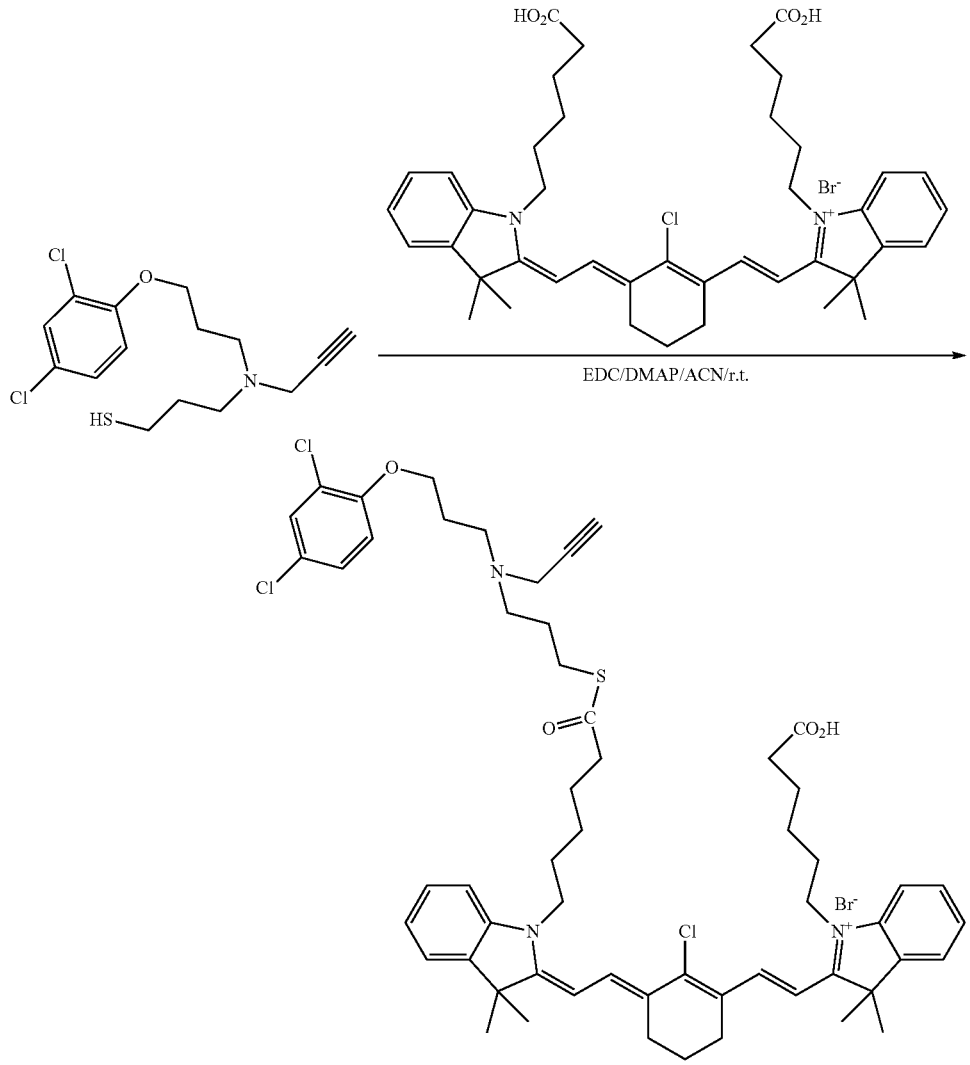

MHI-148 (4.7 mg, 6.2 mmol) and EDC (1.5-2.4 mg, 7.8-12 mmol), followed by 1.5 mg of DMAP (12 mmol) were added into a 20 mL vial equipped with a stir bar. ACN (400 µL) was added to make solution. The reaction mixture of the previous step was transferred dropwise to the vial with 200 µL ACN at room temperature. The reaction mixture was purified by HPLC (GRACE Davison Apollo $C_8$ 5u column, 250 mm×10 mm).

Example 1

MAO A is Expressed in Human Glioma Tissues and Cells

Figure 2:
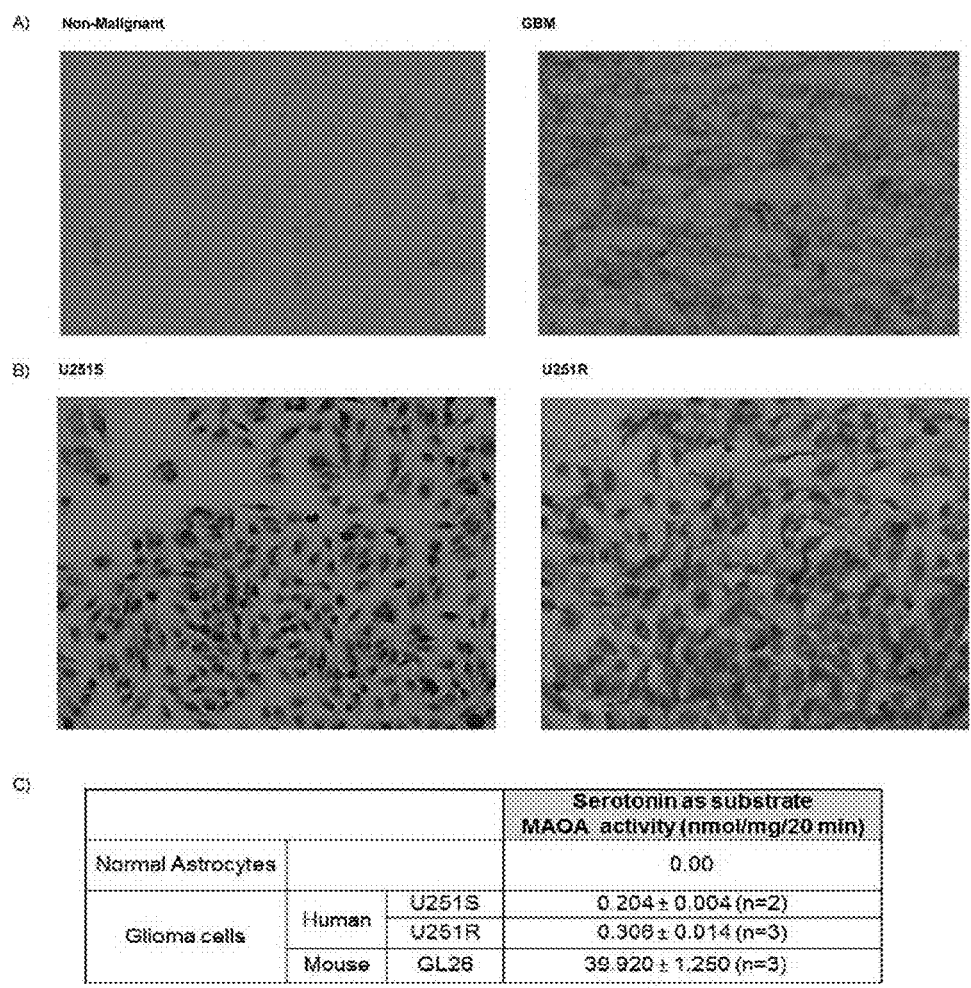
FIG. 2 shows that MAOA expression and activity increased in glioma tissues, mouse and human glioma cells. (A) Non-malignant brain and glioma (GBM) specimens were stained with anti-MAO A. Positive cells are red; nuclei are blue. (B) U251R and U251S cells were stained with anti-MAOA antibody; red staining showed positive cells for MAOA expression. (C) MAO A catalytic activity in U251S and U251R, mouse glioma cells (GL26) and normal astrocytes was measured.

The results show that there is significant staining of MAO A in GBM tissues while no detectable staining was observed in non-tumor brain tissue (FIG. 2A). Based on morphology, the staining in GBM appears to be associated with tumor cells. Human glioma cells, sensitive (U251S) and resistant (U251R), both expressed MAO A as shown by immunostaining (FIG. 2B). These glioma cell cultures were then analyzed for MAO activity (5) using serotonin as substrate (FIG. 2C) and showed that these glioma cells expressed MAO A catalytic activity; in contrast, normal control astrocytes exhibited no detectable MAO A activity.

MAO A activity was also measured in the mouse glioma cell line, GL26; these tumor cells showed high levels of MAO A activity. Based on this information, GL26 cells were chosen to evaluate the inhibitory effects of different MAO inhibitors. Clorgyline and phenelzine inhibited MAO A activity with low $IC_{50}$ of $10^{-9}$ and $10^{-11}$ M, respectively. Tranylcypromine and deprenyl inhibited MAO A activity with $IC_{50}$ value in low micromolar range. This inhibition profile confirmed that indeed MAO A was present in GL26 cells. Taken together, these results showed that MAO A is present in human glioma cells and human GBM tissue but they were not detectable in normal astrocytes.

Example II

MAO A Inhibitor Clorgyline and NMI (Near-infrared Dye Conjugated MAO Inhibitor) Reduced Proliferation, Viability and Migration of TMZ-Sensitive and Resistant Glioma Cells MAO A inhibitors target MAO A expression in both central nervous system and peripheral tissues (9). To target MAO A specifically to brain cancer cells, the MAO inhibitor clorgyline was conjugated to a near infra red (NIR) tumor-specific dye, MHI-148, to produce the novel drug NMI (FIG. 5A) that would preferentially accumulate in cancerous lesions. NMI has been synthesized according to the procedure shown in FIG. 1.

Figure 3:
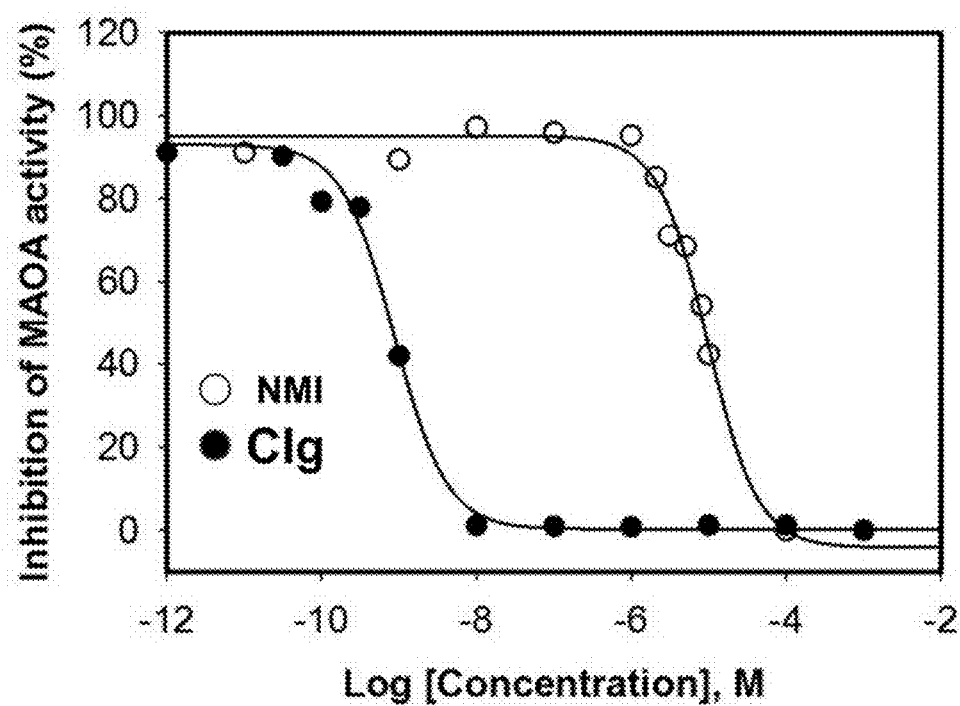
FIG. 3 evidences MAO A inhibition in GL26 cells by Clorgyline and NMI. MAO A activity was determined in GL26 cells in the presence of increasing concentration of clorgyline and NMI. Clorgyline inhibited MAO A activity with $IC_{50}$ value of $10^{-9}$M and NMI inhibited with $10^{-5}$M.
Figure 5:
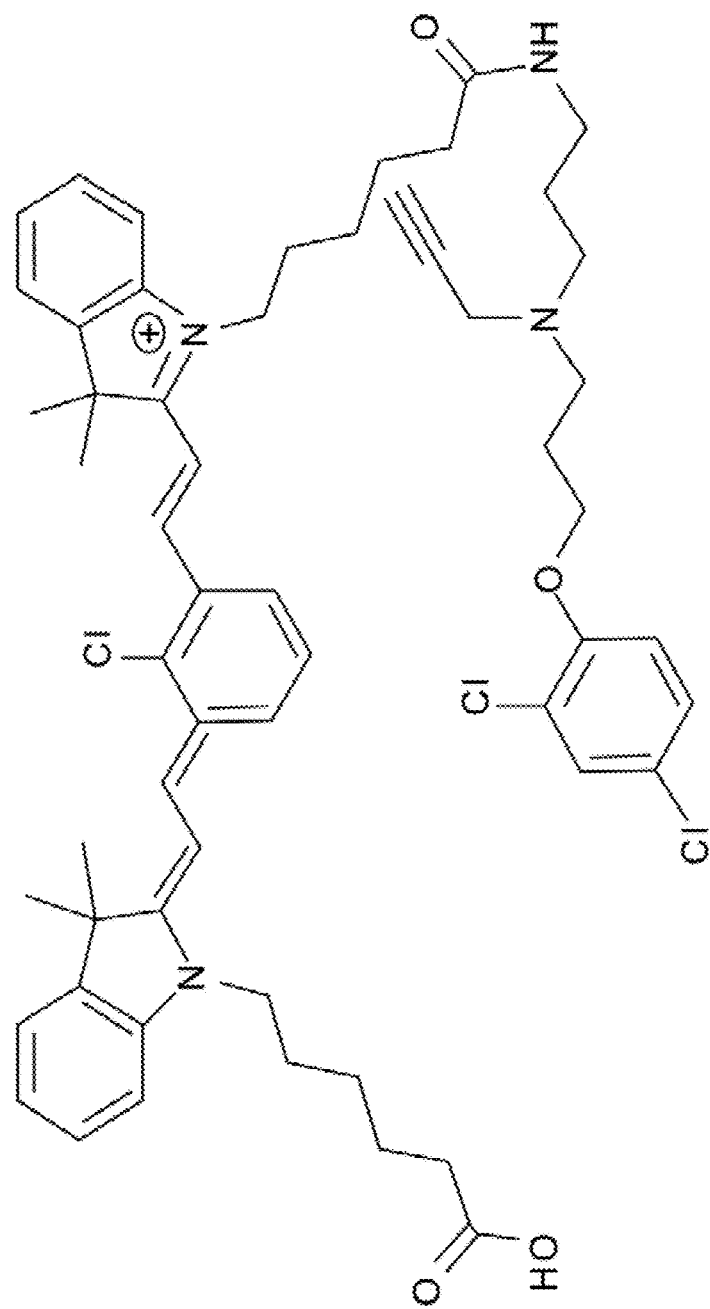
FIG. 5 shows the structure and functions of NMI on human glioma cells. (A) Structure of NMI. (B) Glioma cells treated with NMI. MitoTracker reagent stained mitochondria. (C) Colony formation assays (a) U251S and (b) U251R treated with TMZ (15 μM) (T) and NMI (1, 5, 10 μM) (N) alone and in combination with TMZ for 48 h; colonies were counted. (D) Effect of clorgyline and NMI on cell viability in (a) U251S and (b) U251R as measured by MTS assay. (E) Migration assay was performed on (a) U251S and (b) U251 R cells treated with NMI (1, 5, 10 μM) for 24 h. Error bars=standard error of the mean (SEM); experiments were performed in triplicate. * $p<0.0001$,  $p<0.005$, * $p<0.05$, t-test.
Figure 5:
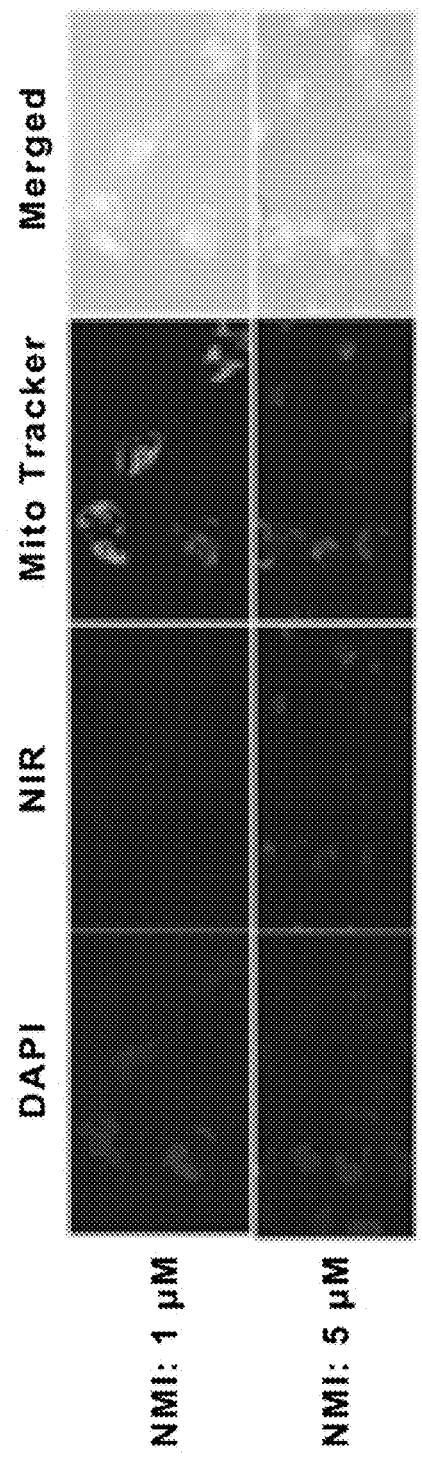
Figure 5:
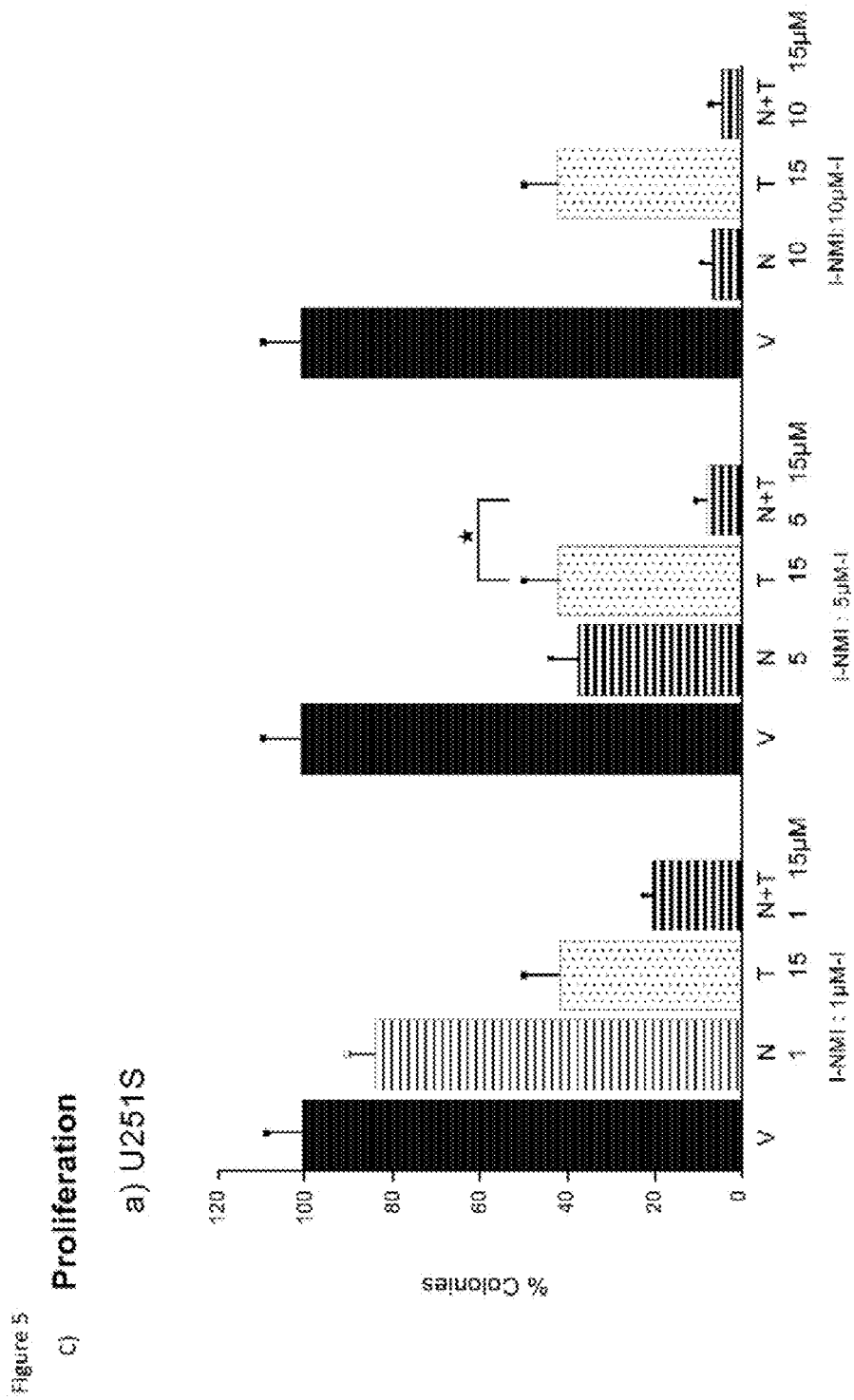
Figure 5:
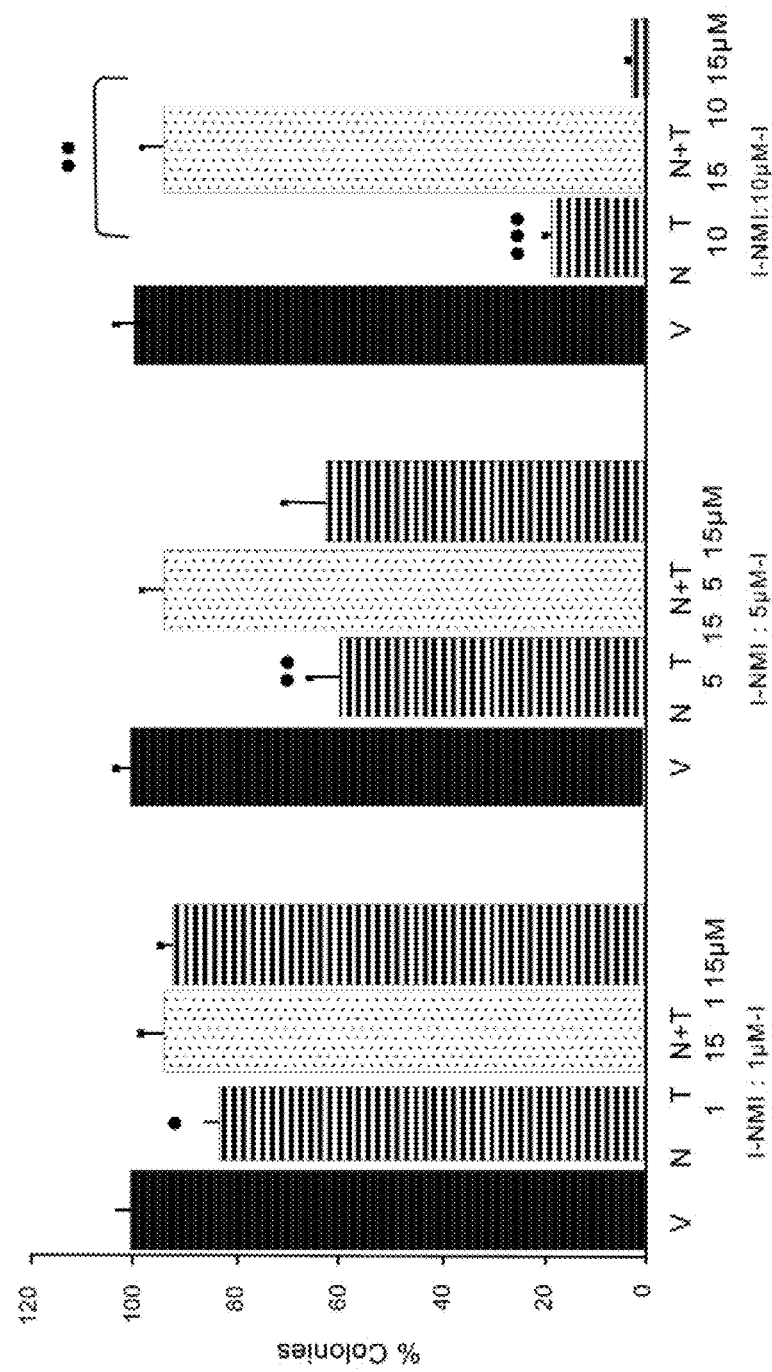

To evaluate the cellular uptake of NMI in human glioma cells confocal microscopy was used. Image analysis of tumor cells treated with NMI (1 µM, 50 µM) showed a significant dose-dependent, uptake compared to vehicle. This compound rapidly accumulated in U251R cells and localized to the mitochondria, as determined by the co-localization of the mitochondria-specific dye, MitoTracker Green (FIG. 5B). The inhibitory effect of NMI on MAO A activity was performed on GL26 mouse glioma cells, which has abundant MAO A activity. The results show that NMI inhibits MAO A with low micromolar $IC_{50}$ (FIG. 3). These results indicate that NMI targeted specifically to glioma cell mitochondria and inhibited MAO A activity in vitro.

Figure 4:
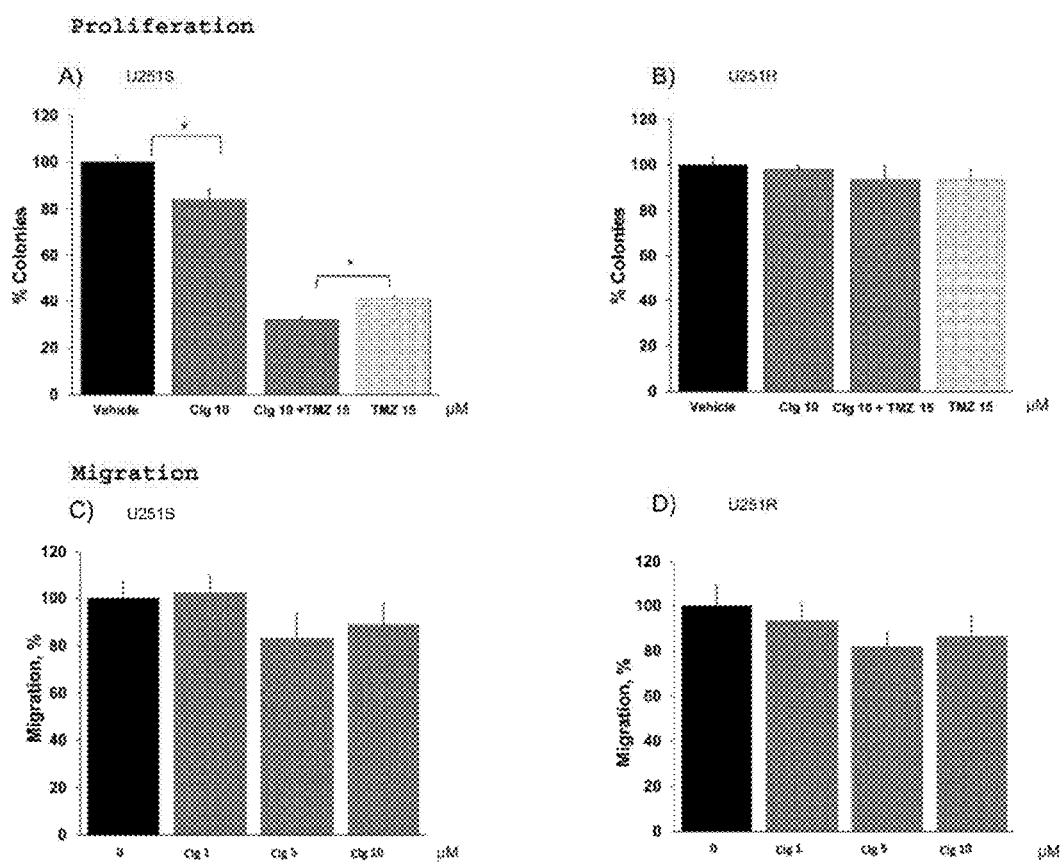
FIG. 4 shows colony formation and migration assays were performed in (A) U251S and (B) U251R with TMZ (15 μM) and Clorgyline (10 μM) alone and in combination with TMZ for 48 h and the colonies were stained with 1% methylene blue on day 8 or 10 and counted. Migration assay was performed in (C) U251S and (D) U251 R cells treated with Clorgyline (1, 5, 10 μM) for 24 and 20 h, respectively. Error bars are ±standard error of the mean (SEM) of experiments performed in triplicate. * $p<0.05$, t-test.

Tumor recurrence is due to the development of TMZ resistance. Therefore, whether clorgyline and NMI is cytotoxic to TMZ-resistant glioma cells using resistant (U251R) glioma cells was investigated. TMZ-sensitive glioma cells (U251S) were used for comparison. For TMZ-sensitive cells, U251S, clorgyline (10 µM) itself reduced the colony formation by 20% (p<0.05) and TMZ (15 µM) by 60%. Combined treatment of clorgyline with TMZ reduced it further to 65% (FIG. 4A). These results indicated that clorgyline increased TMZ sensitivity in drug-sensitive glioma cells (U251S) in vitro.

Treatment of NMI alone in U251S cells at 5 µM and 10 µM reduced colony formation by 60% and 90%, respectively (FIG. 5C (a)). Combine NMI (5 µM) and TMZ (15 µM) reduced colony formation by 90%. (FIG. 5C (a)). These results indicated that NMI increased TMZ sensitivity in drug-sensitive glioma cells (U251S) in vitro.

The effects of NMI on drug-resistant human glioma cell line, U251R were then evaluated. TMZ (µM) has no effect as expected. NMI exhibited a concentration dependent decrease in colony formation at 1, 5 and 10 µM by 20%, 40% and 80%, respectively (FIG. 5C (b)). NMI at 10 µM sensitized the TMZ-resistant cells to TMZ treatment and exhibited greater than a 95% decrease in proliferation. (FIG. 5C (b)). These results showed that NMI sensitized TMZ-resistant cells to TMZ. Clorgyline itself or the combination with TMZ did not show any effect (FIG. 4B).

Cytotoxic effects of clorgyline and NMI on glioma cells were also studied using the MTS assay (FIGS. 5D (a) and (b)); results demonstrated that treatment with clorgyline produced dose response curves with 50% inhibitory concentrations ($IC_{50}$) of approximately 175 µM and 136 µM in U251S and U251R cells, respectively. By contrast, treatment with NMI inhibited cell viability with an $IC_{50}$ value of 5 µM in both cell lines, indicating 30 to 35 fold higher efficacy of NMI as compared to clorgyline. Thus NMI is an effective cytotoxic agent alone or in combination with TMZ in drug-resistant glioma tumor cells.

GBM is a highly invasive tumor; therefore a chemotherapeutic agent that affects tumor cell migration and invasion would be very useful clinically. The ability of NMI to inhibit migration of U251S and U251R cells using the migration assay was studied. Cells were treated with clorgyline (10 µM) and NMI (1, 5 and 10 µM) for 20-24 hours depending upon the time required for complete closure in vehicle treated cells. Clorgyline itself had no effect on the migration rate of human glioma cells (FIGS. 4C & D). However, NMI (5 µM) decreased migration rate by 50% in sensitive cells (U251S) and by 30% in resistant cells (U251R) (FIG. 5E (a) and (b)). These results indicated that NMI is more effective in decreasing the migration rate in U251 TMZ-resistant cells compared to clorgyline.

Example III

Genetically Modified MAO A Knockout (MAO A KO) Animals Exhibited Increased Survival It was determined that MAO A is expressed in human GBM tissues using IHC (FIG. 2B), in contrast to the little staining of MAO A in non-tumor brain. These results showed higher expression of MAO A in glioma cells and GBM tissues suggesting that MAO A may be involved in GBM progression.

Figure 6:
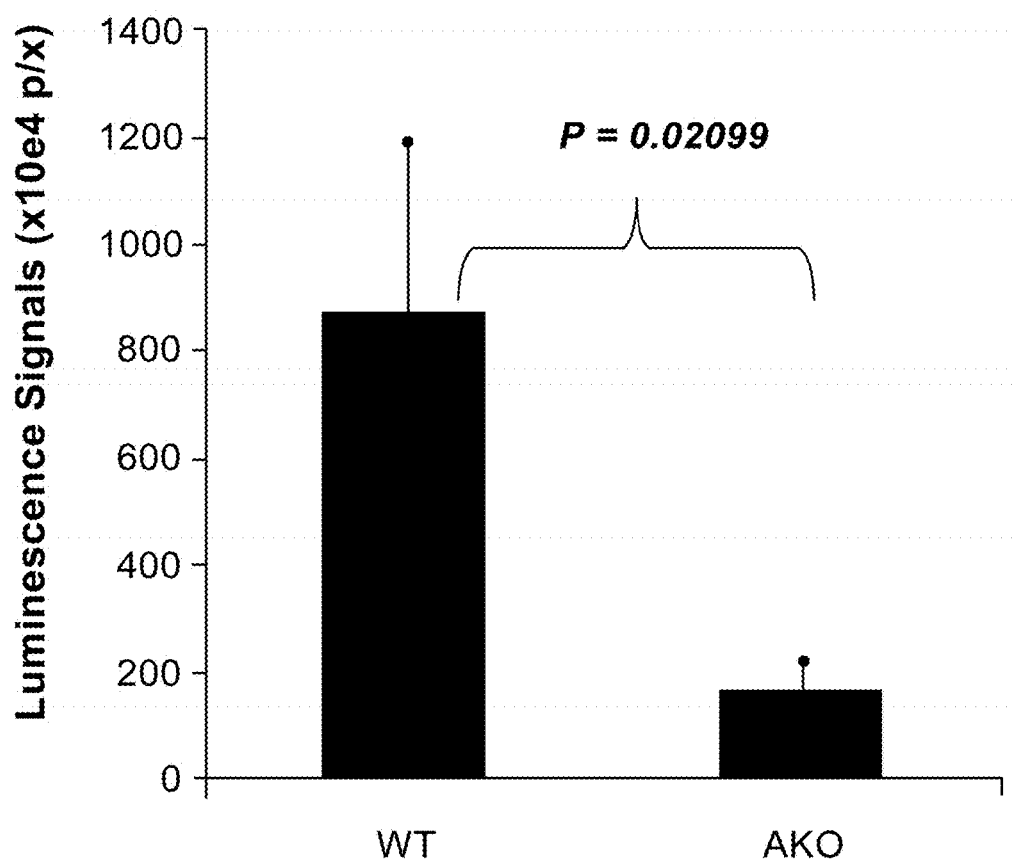
FIG. 6 shows that Glioma progression decreased and survival time increased in MAOA KO mice. (A) Bar graph shows luminescence (correlated with tumor size). (B) Mouse glioma cells were implanted intracranially into WT and MAOA KO; and imaged 10 days later. (mice tag numbers included). (C) Survival of WT and MAOA KO mice (days) were analyzed using Kaplan-Meier plot. (D) Tumor and surrounding tissues were assayed for MAO A activity.
Figure 6:
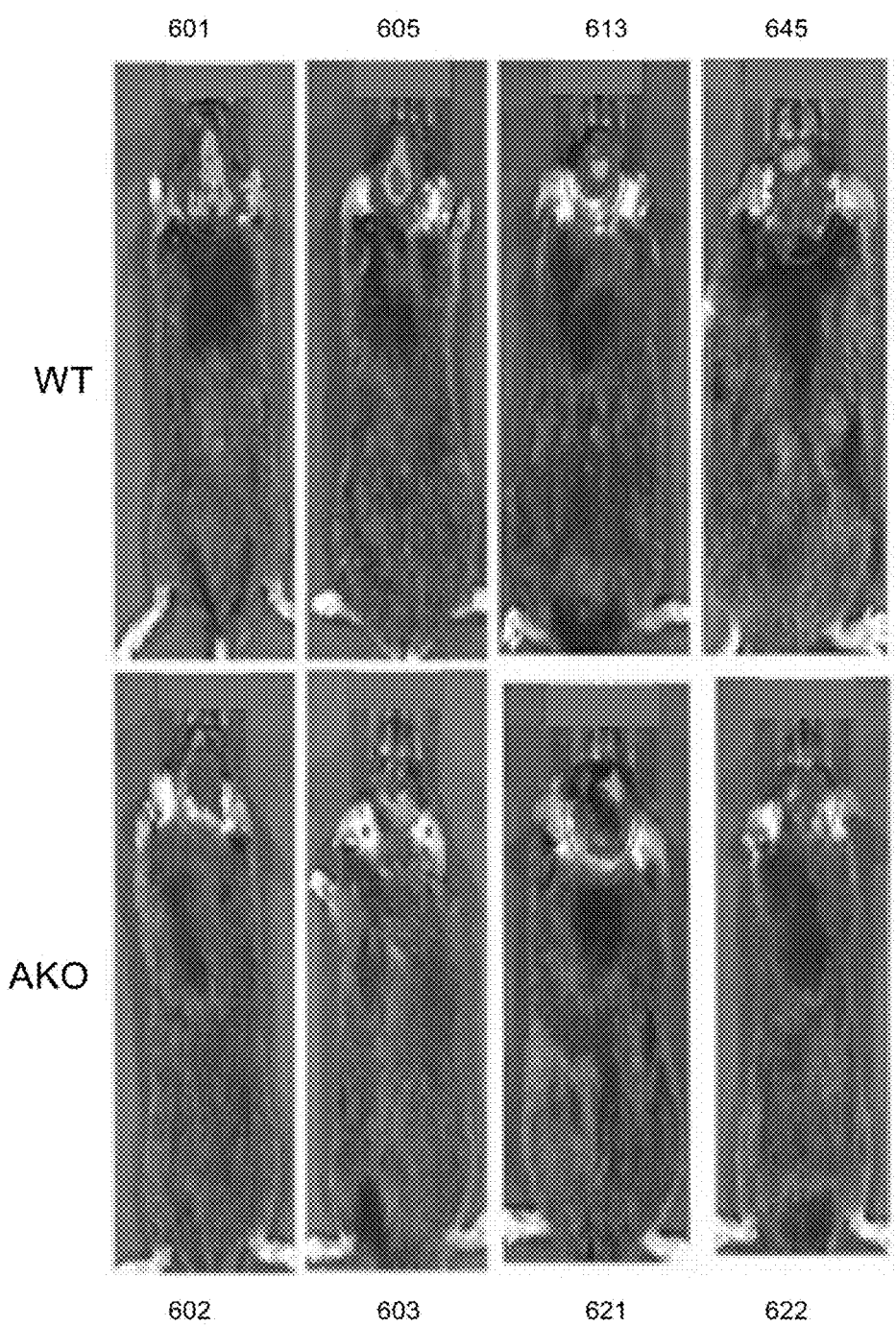
Figure 6:
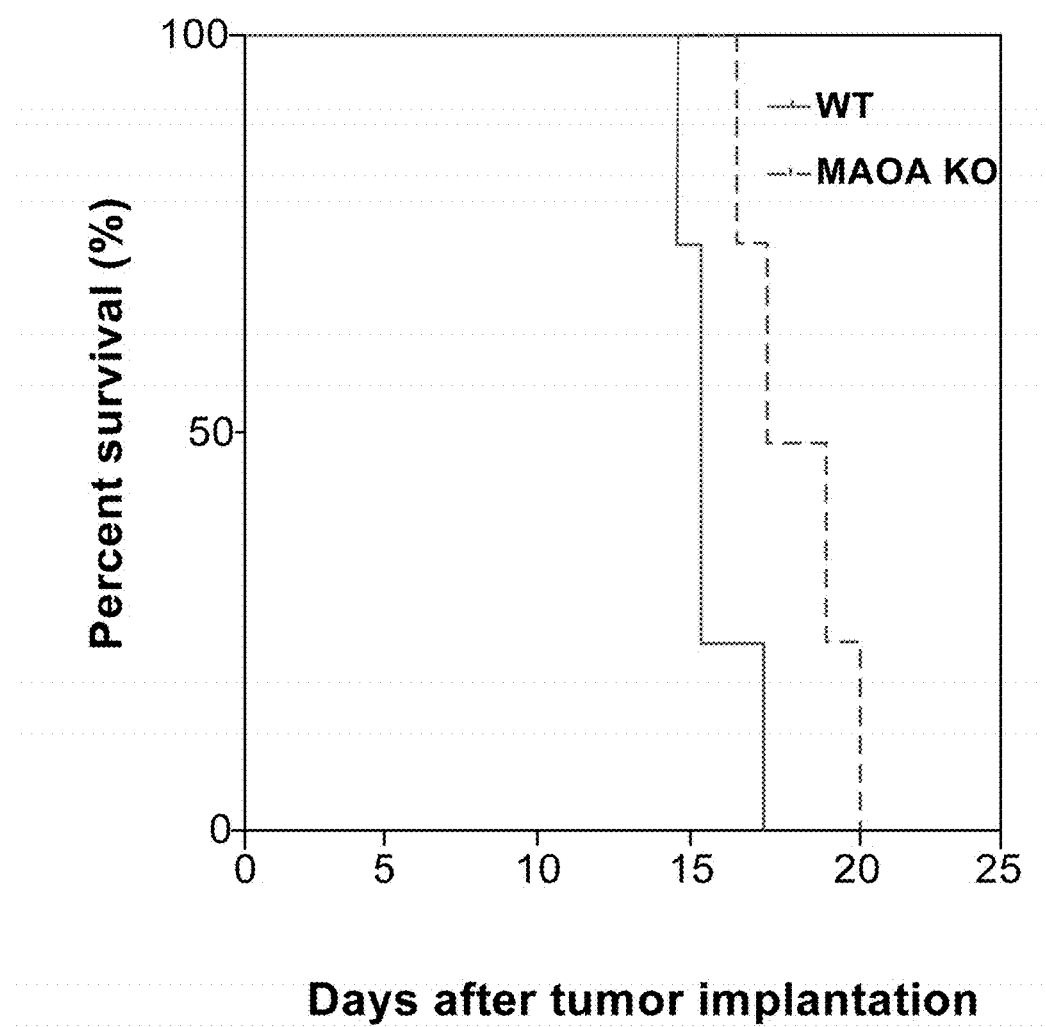

To examine the in vivo effects of MAO A on tumor growth, tumor progression was analyzed in MAO A knock-out mice (KO) in C57bl/6 mice. Mouse glioma cells (GL26)

derived from C57bl/6 mice were used in these studies because these tumor cells showed high levels of MAO A activity (FIG. 2C). The tumor cells were labeled with luciferase and implanted intracranially into MAO A KO and WT C57bl/6 mice; luciferase imaging was performed on day 10. The results showed a 75% reduction in tumor burden (FIGS. 6A and B) and 17.6% (3 days) increase in survival (FIG. 6C).

MAO A activity in the tumor and surrounding tissue of the WT and AKO mice was measured at the end of the experiment. The results show that MAO A KO had low MAO A activity in the tumor tissue as compared to WT. Interestingly, these results indicated that the surrounding tissue with no MAO A activity in KO mice may affect the activity of MAO A in tumor tissue (FIG. 6D). Similar results were obtained with subcutaneous implantations of GL26 tumor cells in MAO A KO and WT mice. These results suggested that a reduction of MAO A in the tumor and tumor microenvironment decreased GBM progression.

Example IV

Figure 7:
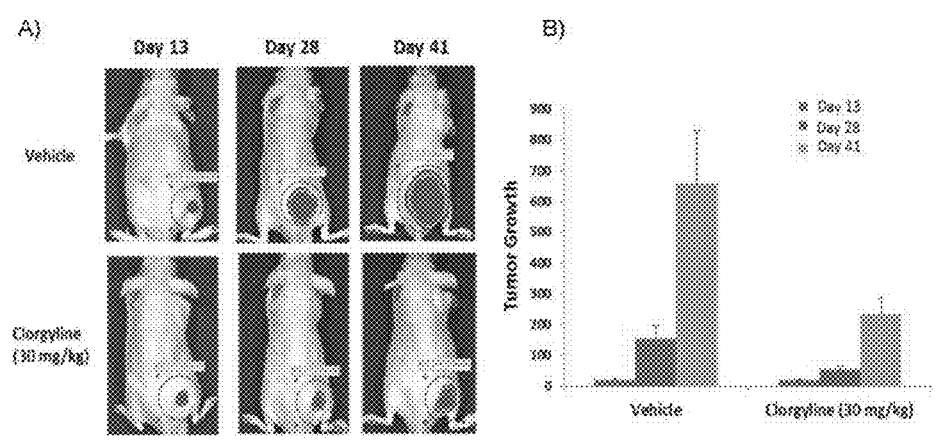
FIG. 7 shows that Clorgyline inhibits glioma growth in mouse xenograft model. (A) Glioma cells were implanted subcutaneously; 7 days later treatment was started: vehicle (water) (30 μl), or clorgyline (30 mg/kg), daily for 21 days. Tumors were imaged on days 13, 28 and 41. (B) Bar graph showed tumor volume as calculated from imaging; $p<0.05$.

Clorgyline Inhibited the Growth of Human Tumor Cells in the Subcutaneous Xenograft Glioma Mouse Model To determine the in vivo effects of clorgyline on tumor progression, U251S luciferase-labeled tumor cells were implanted subcutaneously into nude mice; when tumors were visible by imaging, clorgyline (30 mg/kg), dissolved in sterile water, was administered daily for 21 days. The vehicle control group was treated with water. All mice in treated and control groups showed similar changes in body weight that did not exceed 10% of weight loss, indicating that this treatment regimen was well tolerated. Starting from day 28, the clorgyline-treated groups showed a consistent decrease in tumor growth with 70% decrease at day 41 (FIGS. 7A & 7B). These results demonstrated that inhibition of MAO A reduced tumor growth in vivo.

Example V

Figure 8:
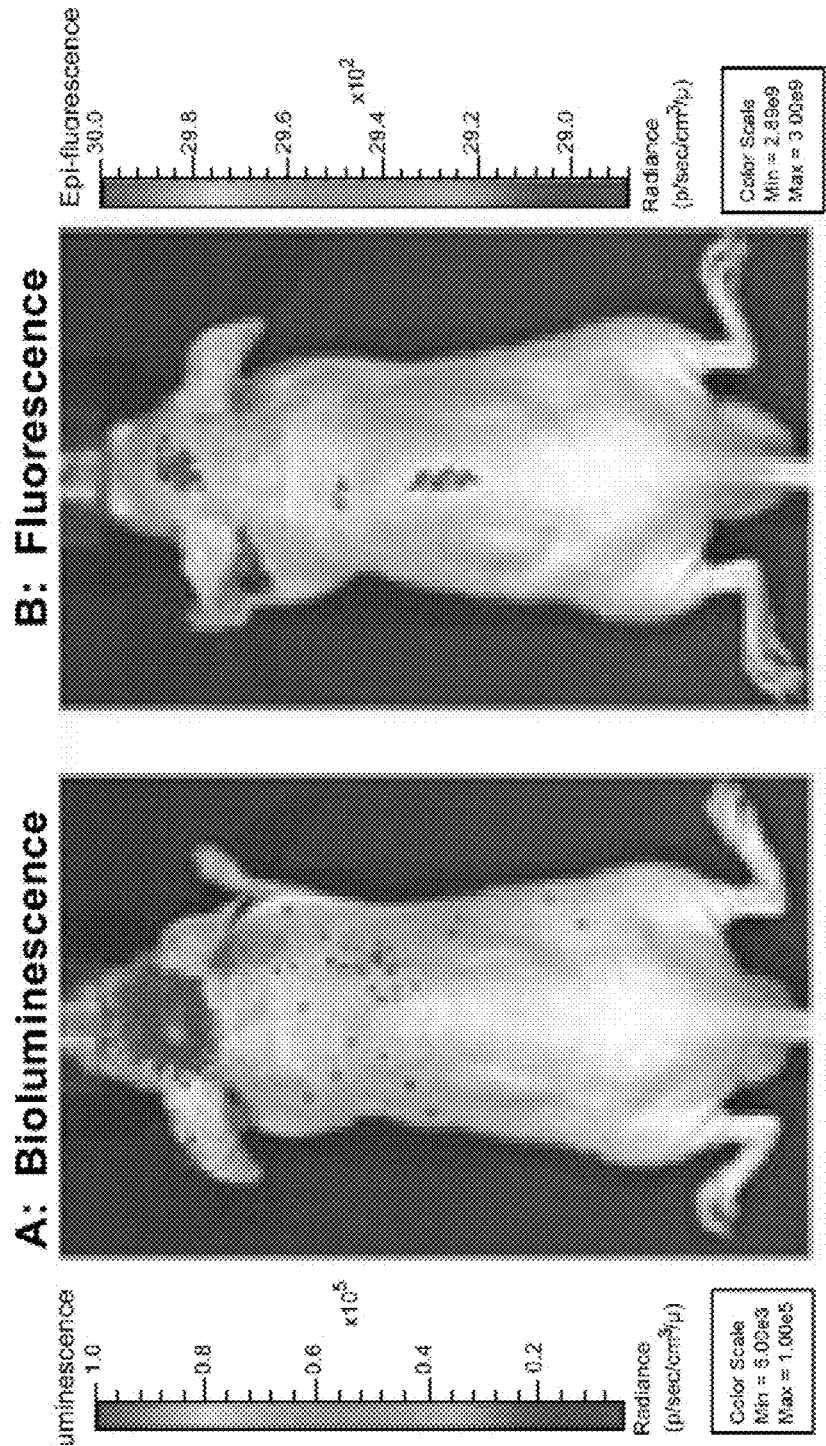
FIG. 8 shows that Clorgyline and NMI alone or in combination with TMZ reduced tumor growth, and increased survival in the intracranial mouse model. Athymic/nude mice were implanted intracranially; with human glioma cells. After 7 days, animals were treated daily for 21 days with: vehicle, TMZ (1 mg/kg), clorgyline (10 mg/kg), TMZ (1 mg/kg)+clorgyline (10 mg/kg), NMI (5 mg/kg), TMZ (1 mg/kg)+NMI (5 mg/kg). TMZ treatment was given for only first 10 days. (A) NMI localizes to tumor. (B) Tumor image 7 days post-implantation, at successive days after treatment. (C) Graph shows luminescence (correlated to tumor size). (D) The Kaplan-Meier survival curve; p values indicate that survival was increased in all treatment groups.
Figure 8:
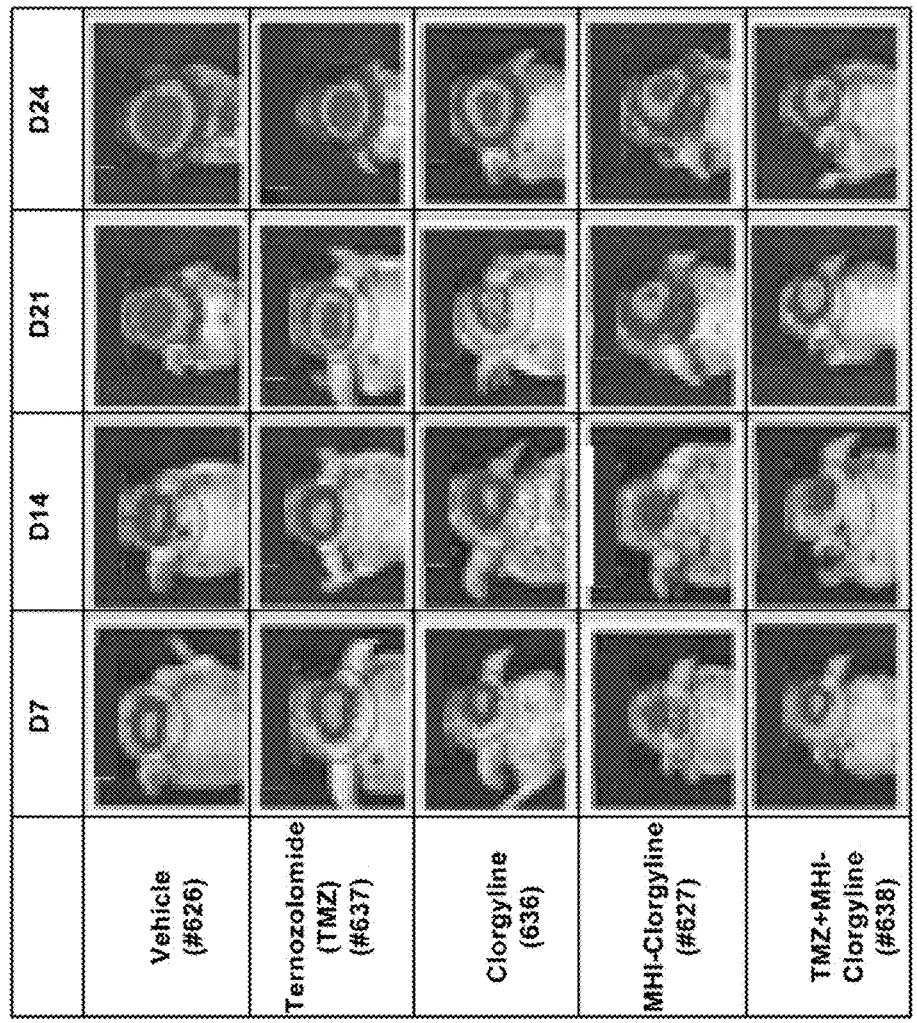
Figure 8:
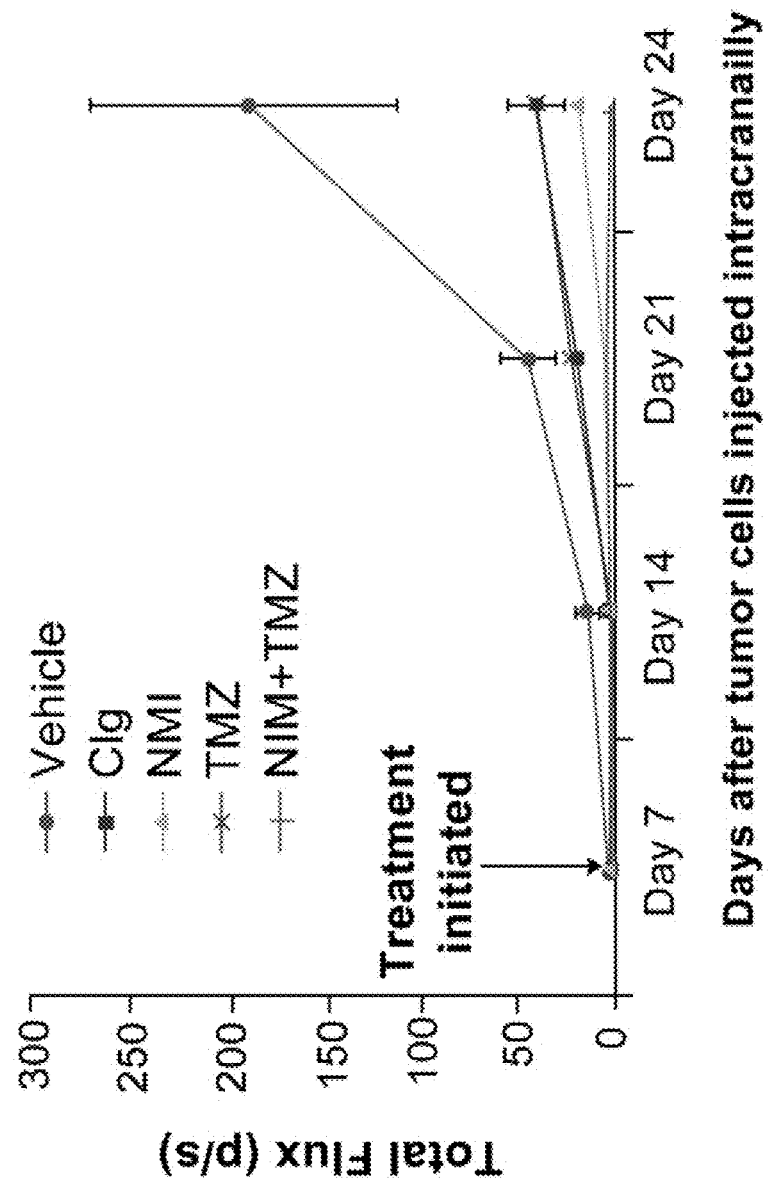
Figure 8:
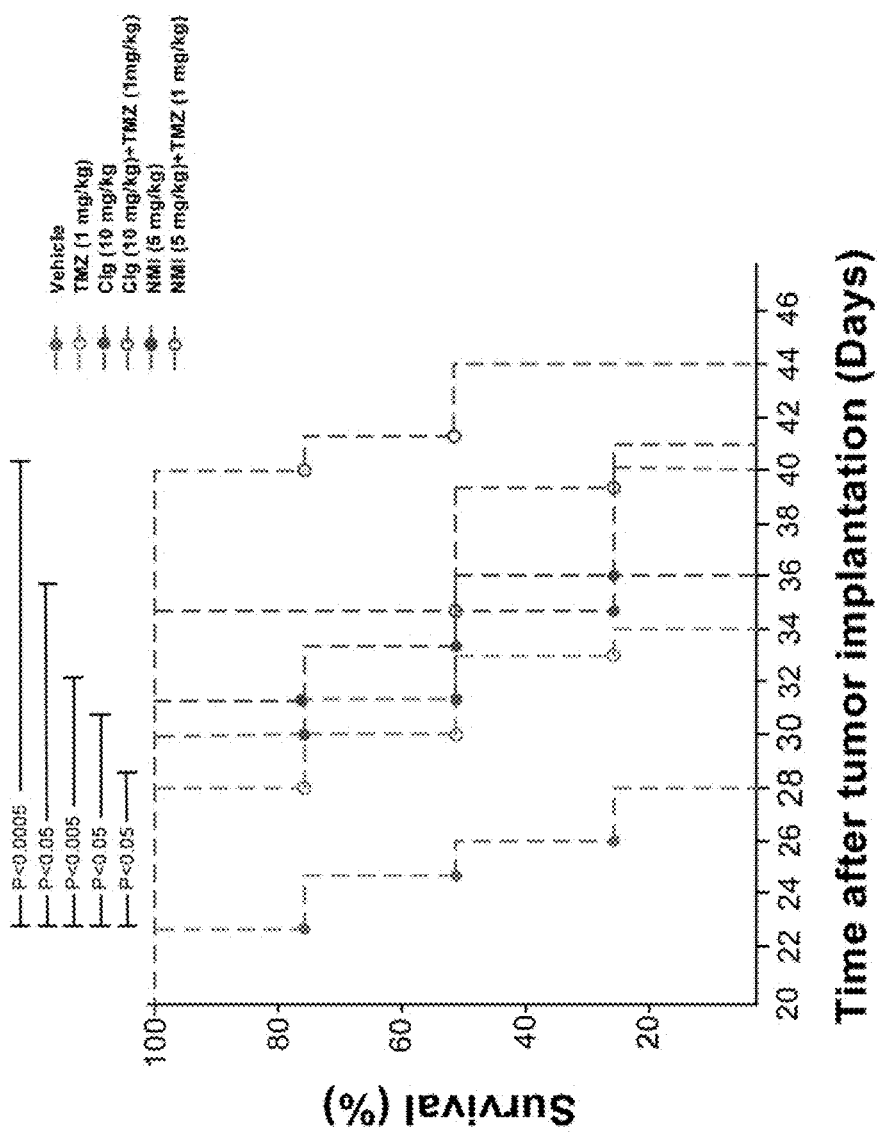

Clorgyline and NMI Increased the Survival Response, Alone or in Combination with TMZ in the Intracranial Mouse Tumor Model To determine whether MAO A inhibitors were also effective against TMZ-resistant glioma cells in vivo, human TMZ-resistant glioma cells (U251R), were implanted intracranially and imaged after 7 days. Mice were then grouped (n=4) and treated with: clorgyline, NMI, TMZ and/or combination of TMZ and clorgyline or NMI. Drugs were administered subcutaneously daily for 21 days except for TMZ, which was administered by oral gavage for 10 days at a dose of 1 mg/kg. Clorgyline was injected at 10 mg/kg and NMI at 5 mg/kg. NIR imaging in vivo showed the specific uptake and accumulation of NMI in glioma cells. Bioluminescence of luciferase-labeled cells as well as fluorescence of NMI was recorded after 10 days of daily subcutaneous injection of NMI (5 mg/kg/day). Overlaying the NIR image with bioluminescence showed that NMI crossed the blood brain barrier, and localized to the tumor site with no detectable distribution throughout the body (FIG. 8A). Animals were imaged on days 7, 14, 21, 24 (FIG. 8B). After 28 days (7 days after implantation and 21 days of treatment) treatment was stopped; tumor growth and survival was documented (FIGS. 8C and 8D). Survival data showed that all animals in the vehicle group died by day 28, animals from the TMZ and clorgyline groups died by 34 ($p<0.05$) and 36 days ($p<0.05$), respectively. The combination treatment of clorgyline with TMZ increased the survival to 40 days from the day of tumor implantation ($p<0.05$). Treatment with NMI alone exhibited increased survival by 12 days (died by day 41, $p<0.005$); and combination of TMZ and NMI increased the survival even further by 16 days (died by day 44, $p<0.005$); the Kaplan-Meier plot showing these data are presented in FIG. 4D. All p values are reported with respect to vehicle. All mice in treated and control groups showed similar changes in body weight that did not exceed 10% throughout the entire duration of experiment. These data indicate that treatment with clorgyline or NMI alone, or NMI in combination with TMZ can delay tumor growth and significantly increase survival time.

Example VI

Figure 9:
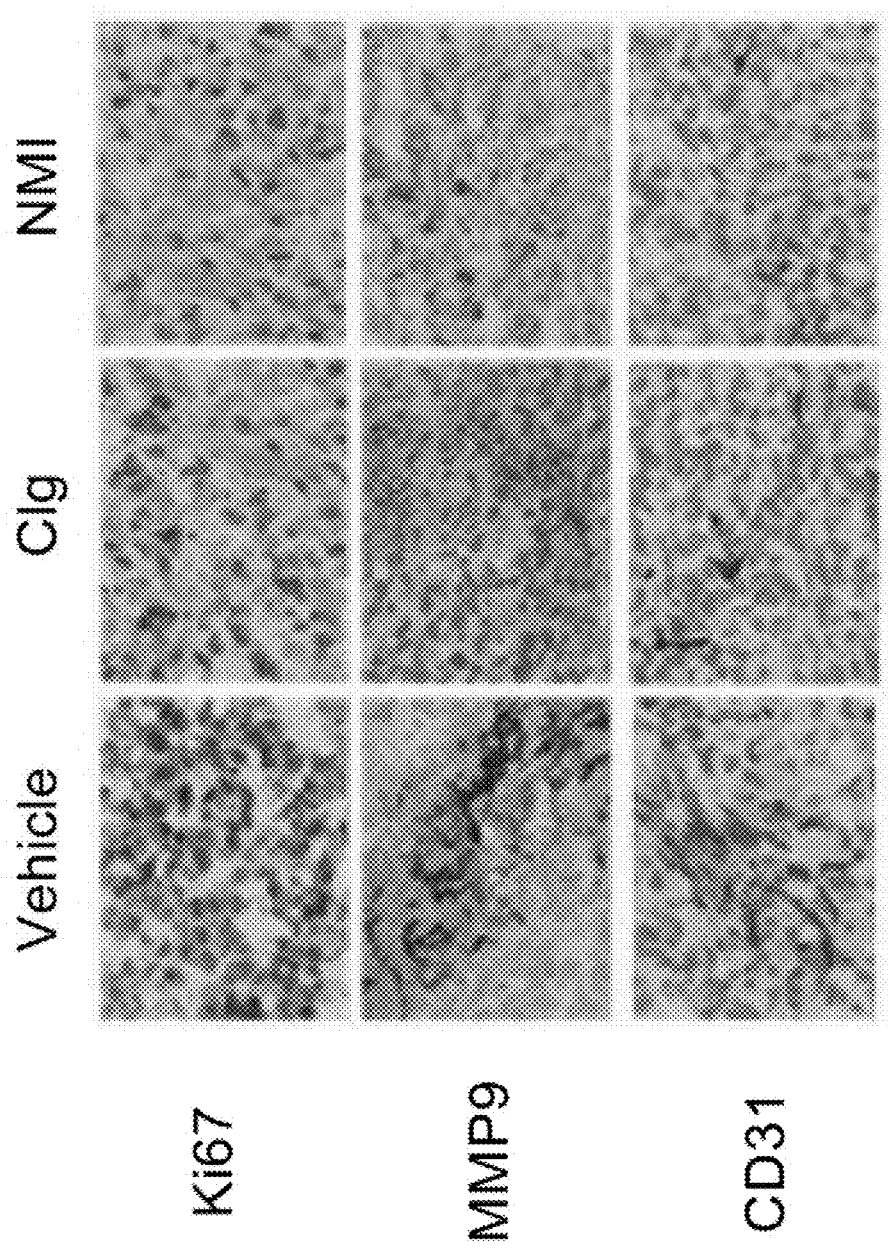
FIG. 9 shows that clorgyline and NMI reduced proliferation and angiogenesis and induced the innate immune response in vivo (A) Tissues from vehicle, clorgyline, and NMI treated animals were immunostained with Ki67, MMP 9 and CD31. Red color indicates positive staining. (mag. 400×). Tissue sections were (B) immunostained for F4/80, TNF-α and TGFβ. Red color indicates positive staining. (mag. 400×). (C) Quantification of Ki67, CD31 and F4/80 in treated tissues. *$p<0.05$, **$p<0.01$ (compared to vehicle).
Figure 9:
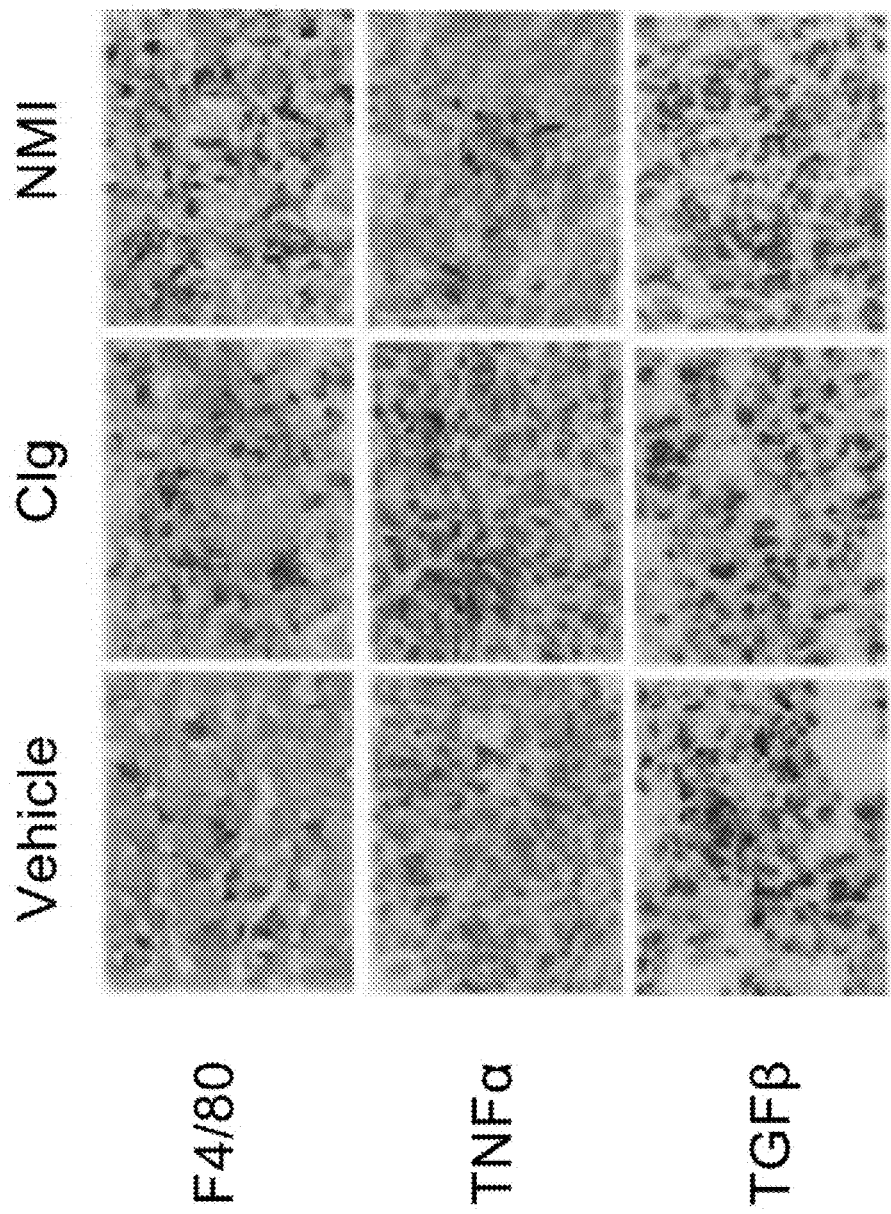
Figure 9:
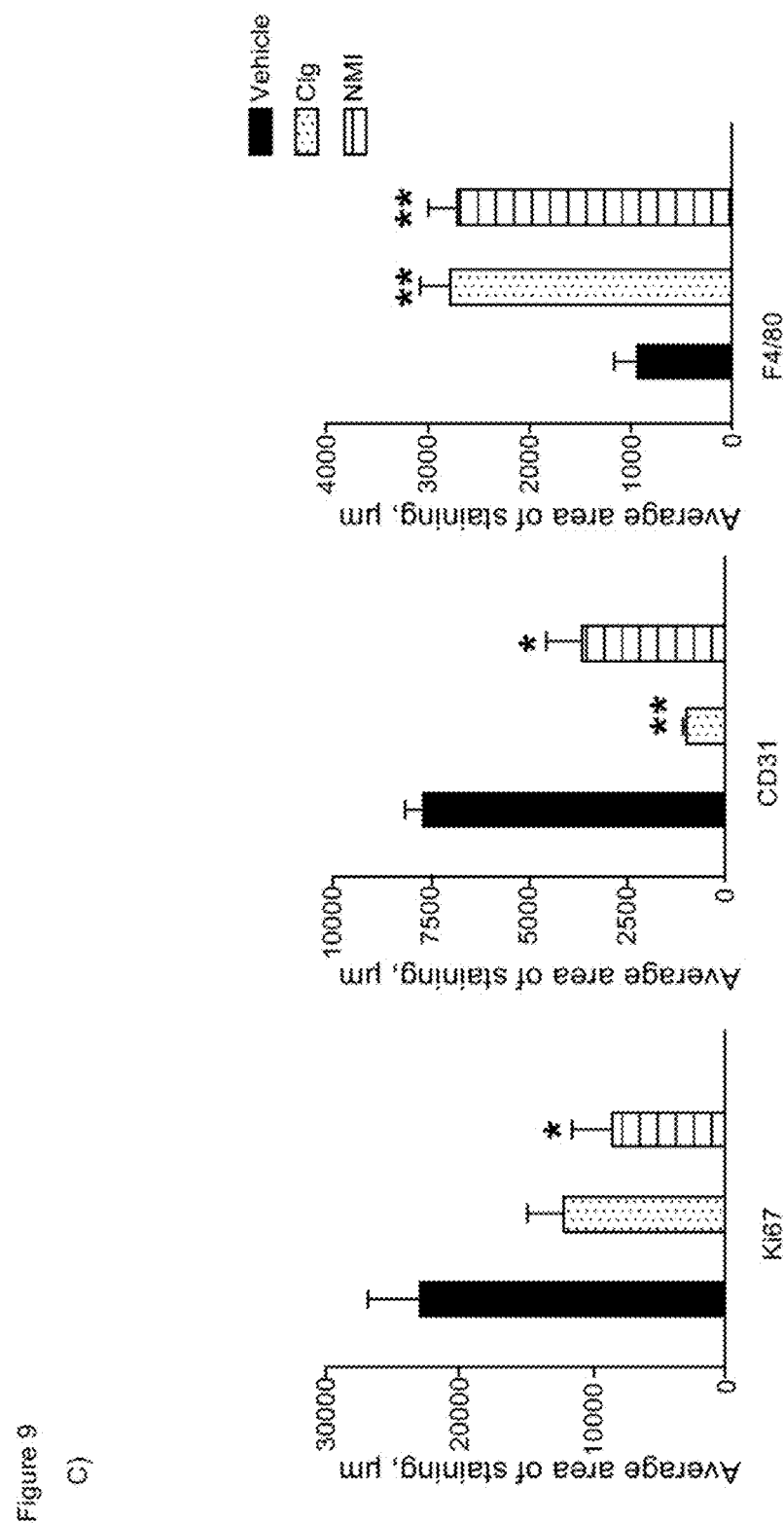

Clorgyline and NMI Reduced Proliferation and Angiogenesis and Induced the Innate Immune Response In Vivo In order to identify potential mechanisms for increased survival of clorgyline or NMI treated animals, tumor tissues were harvested at death, and analyzed for several characteristics including cell proliferation, microvessel density (MVD), inflammatory cell infiltration, and secretion of growth factors. To determine whether cell proliferation was affected by MAO A inhibitors, tumor tissues were stained with Ki67. The results show that the number of positive cells (red precipitate) was decreased in clorgyline and NMI ($p<0.05$, FIG. 9C) treated animals, compared to vehicle-treated animals (FIG. 9A, row 1). Tissues were analyzed for matrix metalloproteinase 9 (MMP9), an enzyme responsible for destruction of extracellular matrix and thereby increasing tumor invasion (13, 14). The results (FIG. 9A, row 2) indicated more positive staining for MMP9 in vehicle tissues as compared to clorgyline or NMI treated animals. These data suggest that MAO inhibitors reduced tumor cell invasiveness. Angiogenesis and blood vessel density, critical for tumor progression (10), were assessed by staining for CD31, endothelial cell marker. The results (FIG. 9A, row 3; FIG. 9C) showed that clorgyline ($p<0.01$) and NMI ($p<0.05$)- treated animals have significantly reduced MVD. These data demonstrated that clorgyline and NMI significantly reduced proliferation, invasion and angiogenesis in tumors, thereby contributing to enhanced survival.

The innate immune response is an important contributor to the regulation tumor growth (11). Therefore, inflammatory cells in the tumors of treated animals were analyzed. Tumor tissues were stained with F4/80, macrophage marker (FIG. 9B, row 1). The results showed a significant increase in macrophages in MAO inhibitor-treated animals as compared to vehicle control ($p<0.01$, FIG. 9C). These data suggested that macrophages may be involved in delayed tumor progression. Inflammatory cytokines are responsible for much of the activity attributed to macrophages. To determine whether the macrophages detected in tumor tissues were proinflammatory, tissue specimens were stained for tumor necrosis factor (TNF)-α, a powerful proinflammatory growth factor. The staining results demonstrated an increased TNF-α positive population in tumors from MAO inhibitor-treated animals (FIG. 9B, row 2). These results suggested that MAO inhibitors upregulate the proinflammatory response, which correlates with macrophage presence and decreased tumor progression (12). Transforming growth factor TGF β, an immune suppressive growth factor, was not affected by MAO A inhibitor treatment (FIG. 9B, row 3); TGF β staining was similar in all three groups. This staining data of tumor tissues provide compelling evidence that clorgyline and NMI inhibitors alter the tumor environment to n reduce tumor growth in vivo.

Example VII

MAO A Inhibitors Increased Animal Survival in the Intracranial Mouse Model

The effects of other MAO A inhibitors on tumor progression were examined. Labeled mouse glioma cells (GL26) were implanted intracranially and imaged 7 days post implantation. Subsequently animals were randomly grouped (n=5); drug treatment groups were TMZ (1 mg/kg), phenelzine (10 mg/kg), phenelzine+TMZ, and moclobemide (10 mg/kg). Phenelzine is an MAO A and B inhibitor; and Moclobemide is an MAO A specific reversible inhibitor. All drugs except for TMZ were administered daily subcutaneously; TMZ was administered orally. Survival data showed that all vehicle-treated animals died by day 12; TMZ and phenelzine ($p<0.05$) groups died by day 14. Phenelzine+TMZ ($p<0.005$) and moclobemide ($p<0.005$)-treated mice died at day 14 and 16, respectively. The Kaplan-Meier plot showing these data are presented in FIG. 10A. All p values are reported with respect to vehicle. These results showed that phenelzine in combination with TMZ and moclobemide increased survival.

Figure 10:
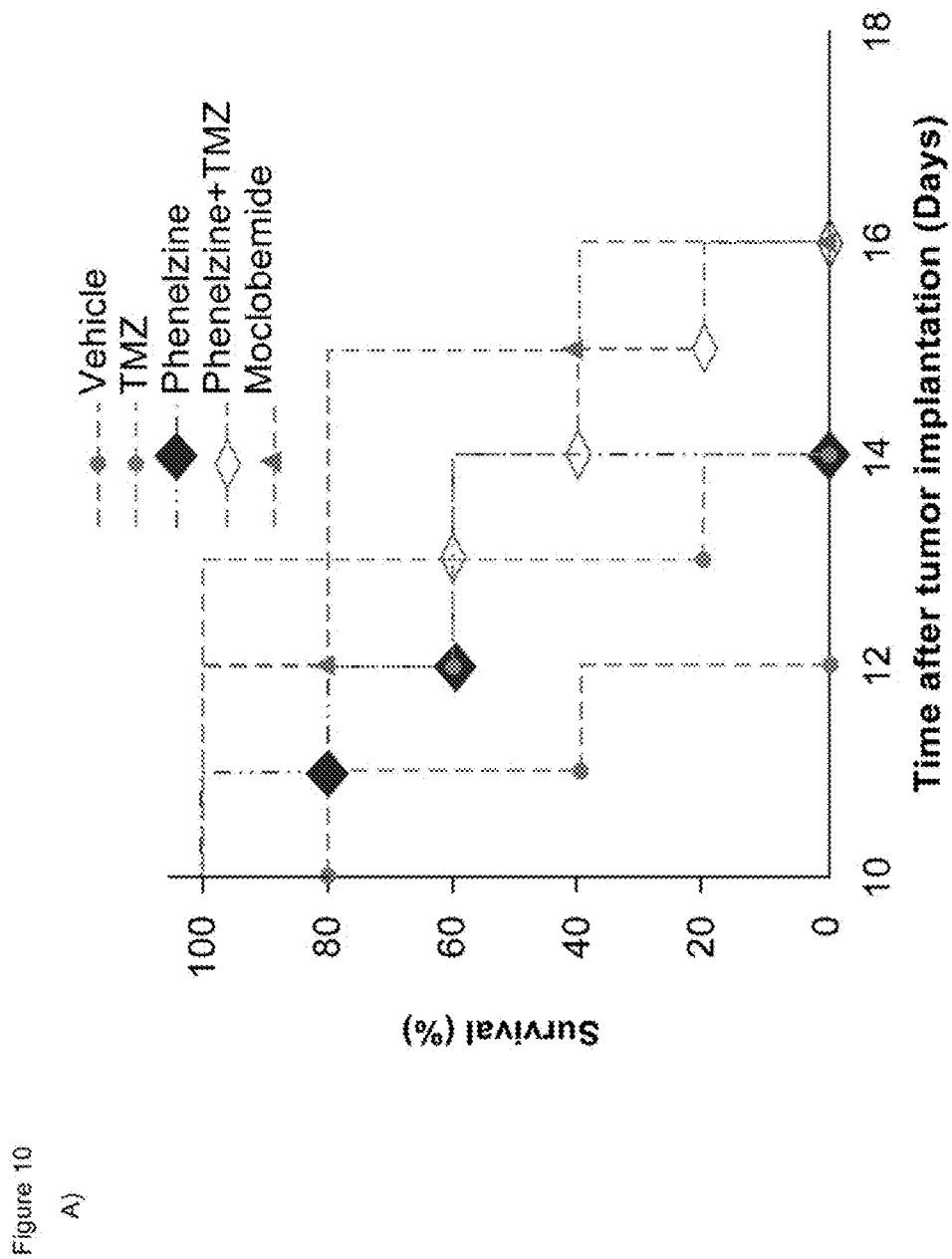
FIG. 10 shows that MAO A inhibitors reduce tumor growth, MAOA activity and increase animal survival. A) mouse glioma cells were implanted intracranially: after 6 days, animals were treated daily with vehicle, TMZ (1 mg/kg), phenelzine (10 mg/kg), TMZ (1 mg/kg)+phenelzine (10 mg/kg) and moclobemide (10 mg/kg). Survival was analyzed using the Kaplan-Meier plot; p values indicate that all treatments significantly increased survival. B) MAOA activity was reduced after treatment with MAO inhibitors.
Figure 13A:
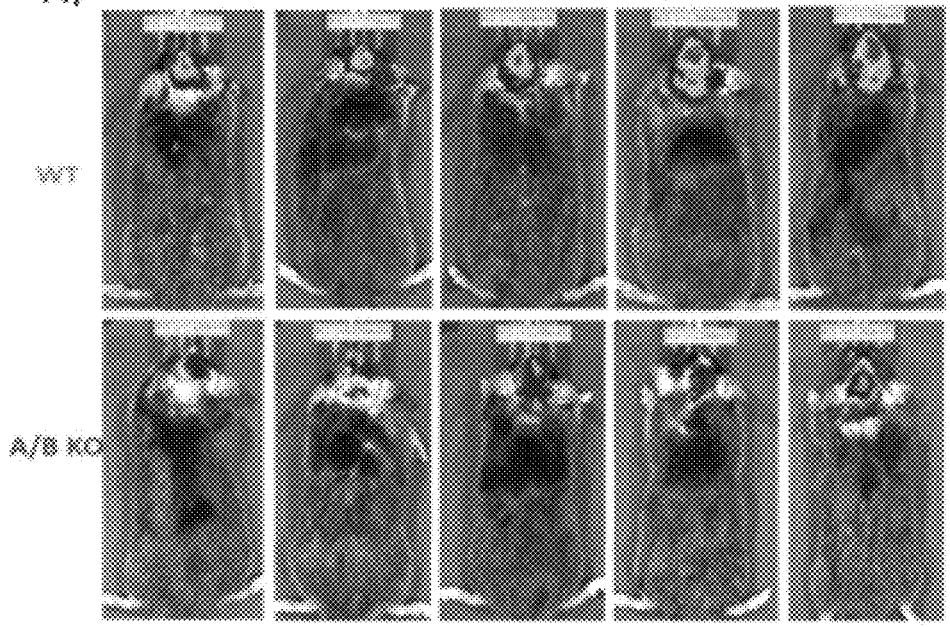
FIGS. 13A-13C show that glioma growth is significantly decreased in MAOA/B knockout (KO) mice. A) Luciferase-labeled GL-26 glioma cells were implanted intracranially into WT and A/B KO C57 B/L mice and imaged after 10 days. B) Bar graph depicts the luminescence which correlated with tumor size. C) Comparison of animal survival of WT and MAOA/B KO mice. Survival rate was increased by 116.6% (14 days). ***$p<0.0001$.
Figures 13B, 13C:
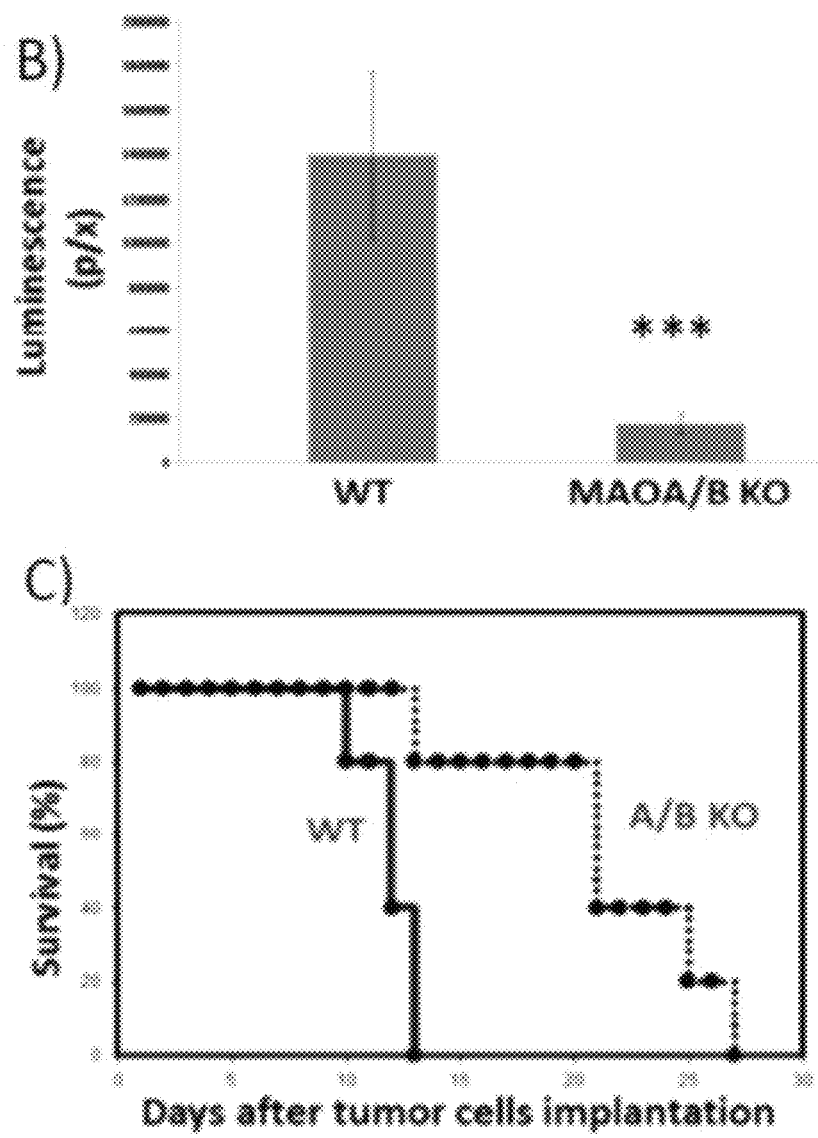
Figure 14:
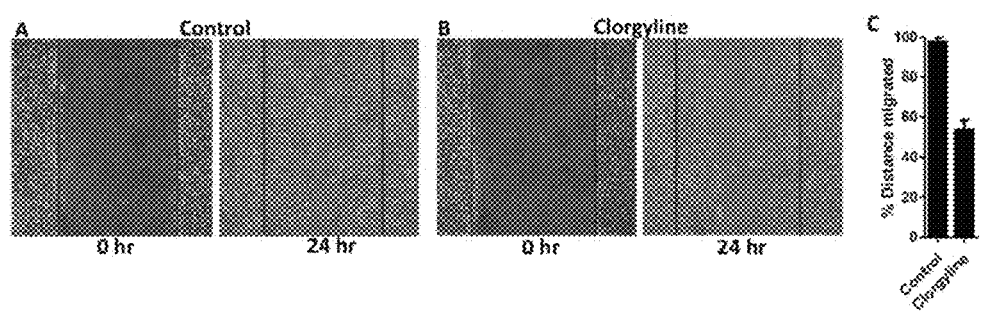
FIG. 14 shows that treatment of human glioma cells with clorgyline decreases glioma cell migration. Glioma cells (LN229) were grown to confluency, and then treated with mitomycin C to prevent proliferation. A "scratch" was made to clear an area of cells; then cultures were treated with (A) vehicle or (B) clorgyline [10 μM] for 24 hrs. The results show that clorgyline decreased the rate of migration by approximately 50%. (C) Summary of data.
Figure 15:
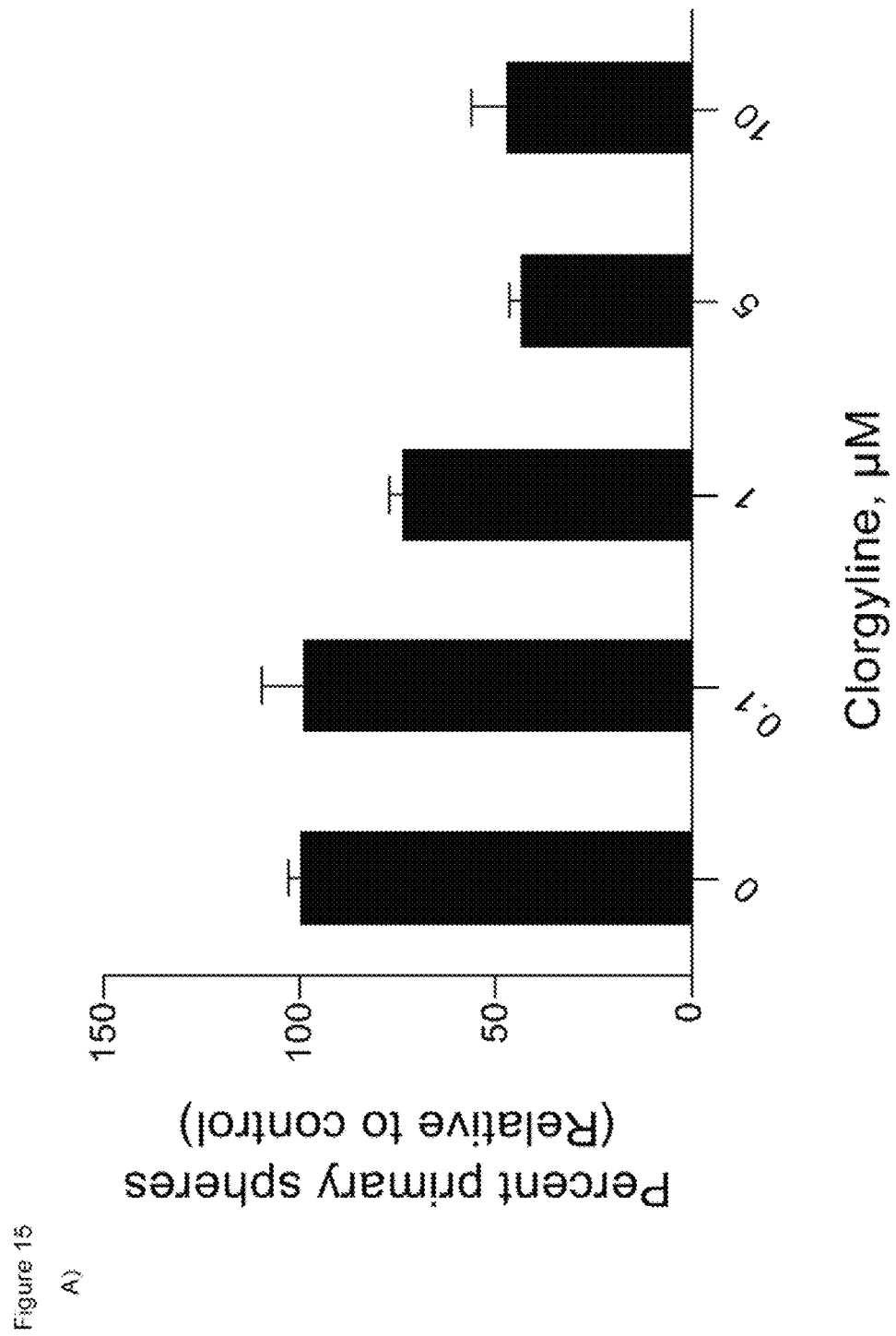
FIG. 15 shows that treatment with the MAO A inhibitor, clorgyline, induces glioma stem cell cytotoxicity. (A) GSC were treated with clorgyline for 96 hrs and assayed using sphere formation; (B) GSC were treated with clorgyline and TMZ for 72 hrs, clorgyline was added again for another 48 hrs and assayed (MTT). Results show that clorgyline is cytotoxic for glioma stem cells at 5 and 10 μM. Furthermore, clorgyline in combination with TMZ exhibits a 50% increase in cytotoxicity.
Figure 15:
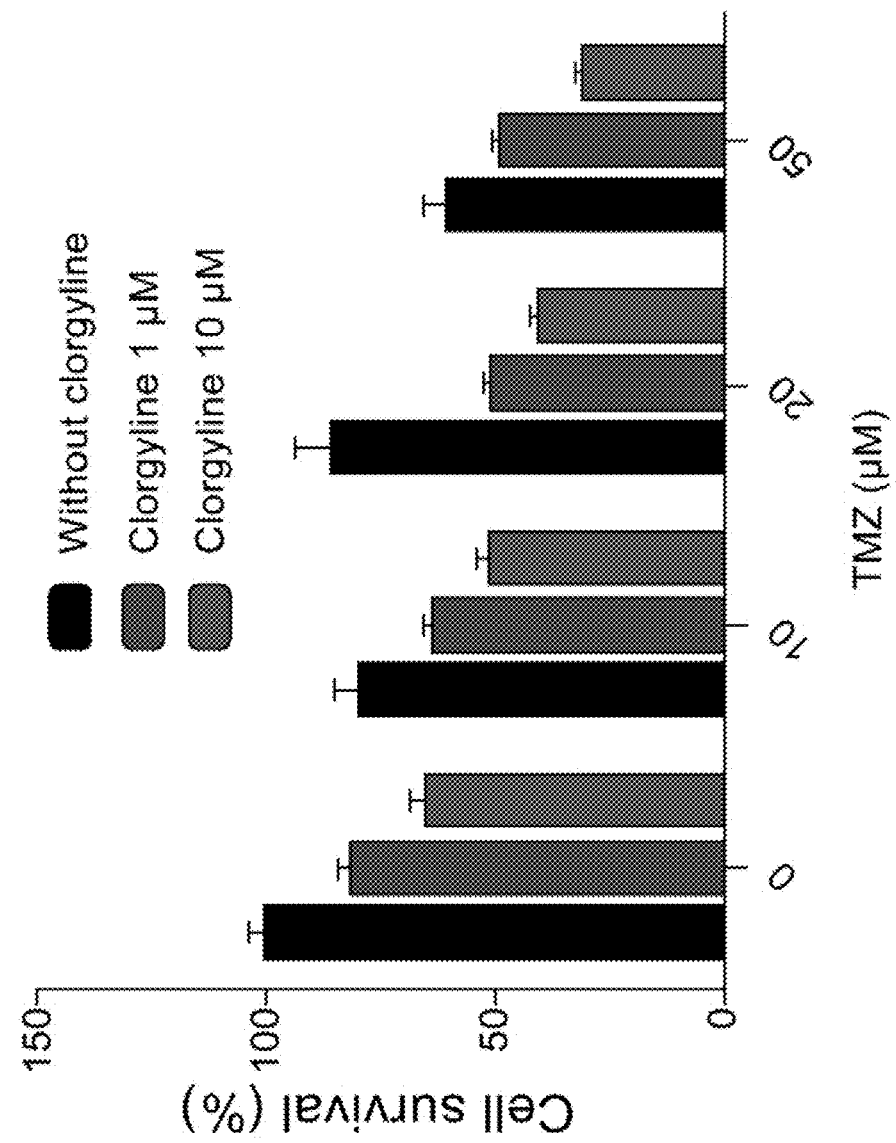
Figure 16:
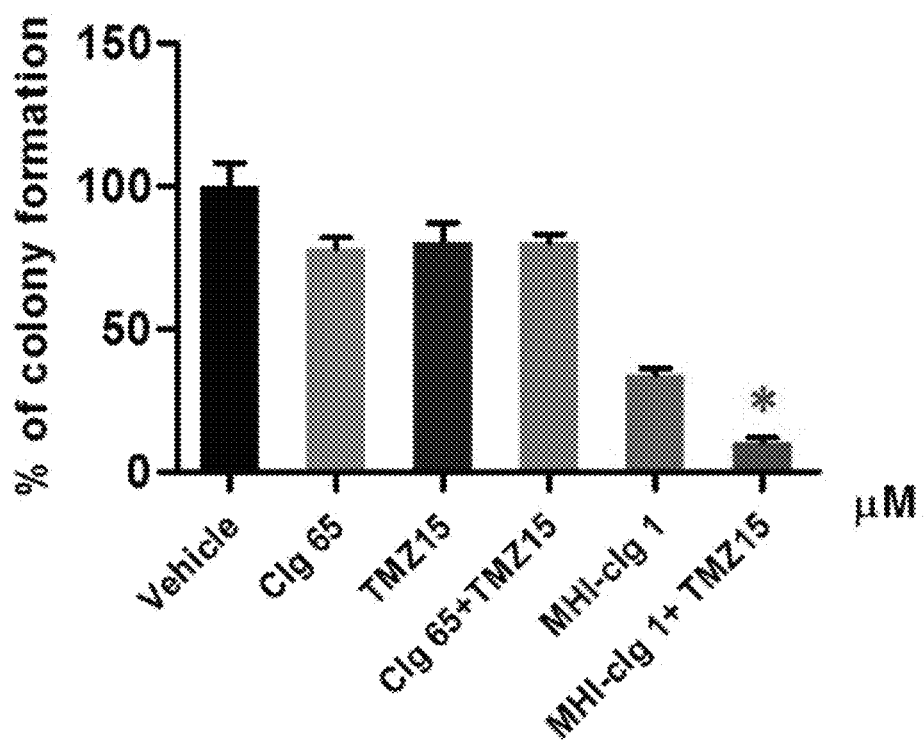
FIG. 16 shows that MHI-Clorgyline Reduces Colony Formation in Temozolomide-Resistanl Glioma Cells. U251 TMZ resistant (R) were plated in 6-well plates and treated with MAOA inhibitors and TMZ for 48 hrs. MHI-Clorgyline reduces the colony formation (CFA) rate by 65% as compare to vehicle. Combined treatment of TMZ and MHI-Clorgyline sensitizes TMZ-resistant glioma cells to TMZ, resulting in reduced colony formation by 85%. CFA is a measure of cell death; the fewer colonies the more cell death.
Figure 17:
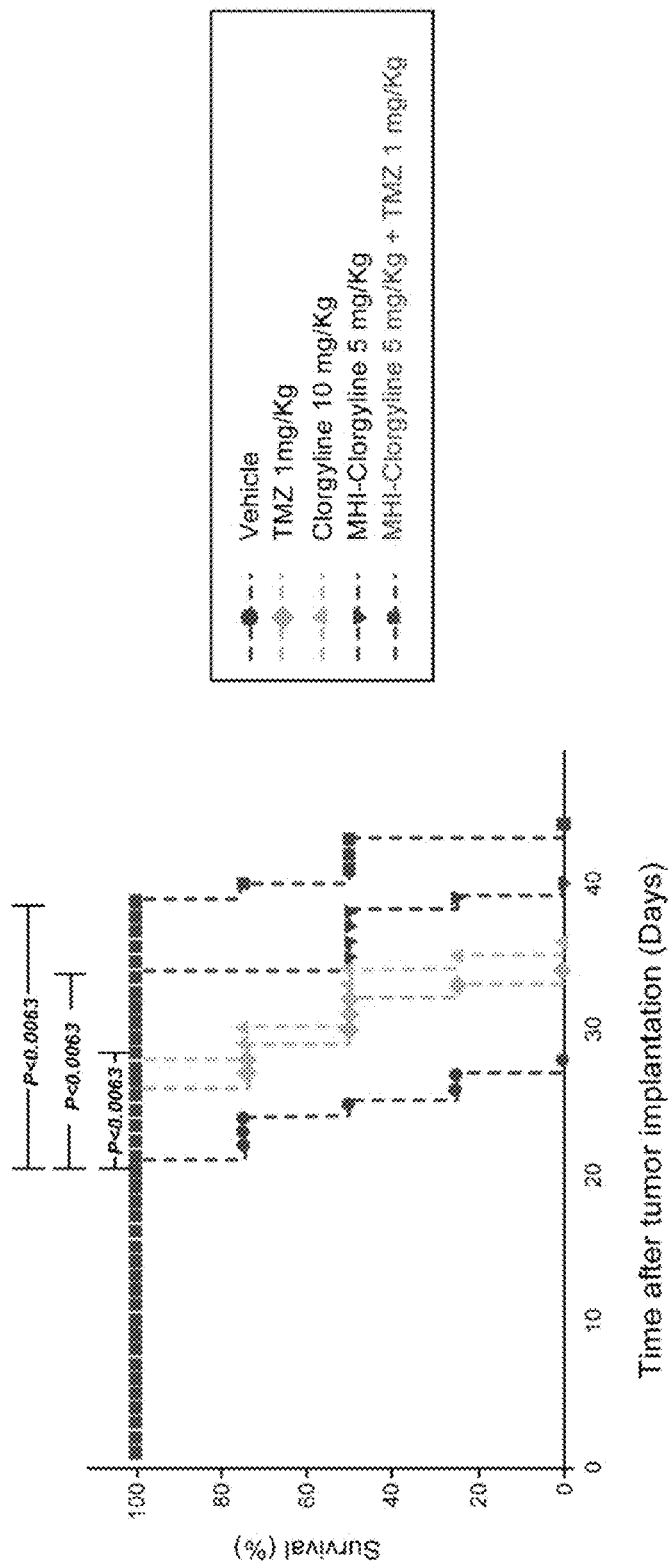
FIG. 17 shows that the administration of MHI-Clorgyline alone or in combination with temozolomide (TMZ) increases survival in animals bearing intracranial TMZ-resistant gliomas. Athymic/nude mice were implanted intracranially with U251-TMZ-resistant glioma cells. After 7 days, animals were separated into the following groups and treated daily: vehicle, TMZ (1 mg/kg), Clorgyline (10 mg/kg), MHI-Clorgyline (5 mg/kg), or TMZ (1 mg/kg)+ MHI-Clorgyline (5 mg/kg). After 21 days, treatment was stopped; survival was documented. The results showed that MHI-Clorgyline-treated animals survived 50% longer than the vehicle treated animals (p<0.0001), and TMZ+MHI-Clorgyline-treated mice survived 70% longer than vehicle (p<0.00001). Inhibition of MAOA using MHI-Clorgyline alone or in combination with TMZ is effective in decreasing glioma tumor progression. MHI-Clorgyline sensitizes TMZ-resistant cells to TMZ.

To better understand the role of MAO activity in tumor progression, brain tissues were harvested, and analyzed for MAO A activity. Phenelzine and moclobemide exhibited 87% and 62% reductions in enzyme activity, respectively (FIG. 10B). These results indicated that the increase in survival correlates with decreased MAO A activity.

Example VIII

Further Results Supporting the Unexpected Nature of the Present Invention

FIG. 18 discloses data indicating that prostate cancer and glioma have MAO A activity and can be treated with MAO I and MHI-clorgyline, whereas pancreatic cancer and lymphoma do not have MAO A activity, thus cannot be treated by clorgyline and MHI-clorgyline.

FIG. 19 demonstrates that clorgyline and MHI-clorgyline both induce stem cell cytotoxicity and MHI-clorgyline is more effective than clorgyline by itself.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

The following references are each relied upon and incorporated herein in their entirety.

1. Stupp R, Hegi M E, Mason W P, van den Bent M J, Taphoorn M J B, Janzer R C, et al. Effects of radiotherapy with concomitant and adjuvant temozolomide versus radiotherapy alone on survival in glioblastoma in a randomised phase III study: 5-year analysis of the EORTC-NCIC trial. Lancet Oncol. 2009; 10:459-66.
2. Stupp R, Mason W. Radiotherapy plus concomitant and adjuvant temozolomide for glioblastoma. New Engl J Med. 2005; 352:987-996.
3. Wu J B, Shao C, Li X, Li Q, Hu P, Shi C, et al. Monoamine oxidase A mediates prostate tumorigenesis and cancer metastasis. J Clin Invest. 2014; 124:2891-908.
4. Jhaveri N, Cho H, Torres S, Wang W, Schönthal A H, Petasis N A, et al. Noscapine inhibits tumor growth in TMZ-resistant gliomas. Cancer Lett. 2011; 312:245-52.
5. Chen K, Ou X-M, Chen G, Choi S H, Shih J C. R1, a novel repressor of the human monoamine oxidase A. J Biol Chem. 2005; 280:11552-9.
6. Virrey J J, Golden E B, Sivakumar W, Wang W, Pen L, Schönthal A H, et al. Glioma-associated endothelial cells are chemoresistant to temozolomide. J Neurooncol. 2009; 95:13-22.
7. Scott A L, Bortolato M, Chen K, Shih J C. Novel monoamine oxidase A knock out mice with human-like spontaneous mutation. Neuroreport. 2008; 19:739-43.
8. Cho H-Y, Wang W, Jhaveri N, Torres S, Tseng J, Leong M N, et al. Perillyl alcohol for the treatment of temozolomide-resistant gliomas. Mol Cancer Ther. 2012; 11:2462-72.
9. Shih J C, Chen K, Ridd M J. Monoamine oxidase: from genes to behavior. Annu Rev Neurosci. Annual Reviews; 1999; 22:197-217.
10. Hanahan D, Weinberg R A. The Hallmarks of Cancer. Cell. 2000; 100:57-70.
11. Hagerling C, Casbon A-J, Werb Z. Balancing the innate immune system in tumor development. Trends Cell Biol. Elsevier; 2014. In press
12. Lamagna C, Aurrand-Lions M, Imhof B A. Dual role of macrophages in tumor growth and angiogenesis. J Leukoc Biol. 2006; 80:705-13.
13. Stetler-Stevenson W G, Yu A E. Proteases in invasion: matrix metalloproteinases. Semin Cancer Biol. 2001; 11:143-52.
14. Duffy M J, Maguire T M, Hill A, McDermott E, O'Higgins N. Metalloproteinases: role in breast carcinogenesis, invasion and metastasis. Breast Cancer Res. 2000; 2:252-7.
15. Hodorová I, Rybárová S, Vecanová J, Solár P, Domoráková I, Adamkov M, et al. Comparison of expression pattern of monoamine oxidase A with histopathologic subtypes and tumour grade of renal cell carcinoma. Med Sci Monit. 2012; 18:BR482-6.
16. True L, Coleman I, Hawley S, Huang C-Y, Gifford D, Coleman R, et al. A molecular correlate to the Gleason grading system for prostate adenocarcinoma. Proc Natl Acad Sci USA. 2006; 103:10991-6.

17. Rybaczyk L A, Bashaw M J, Pathak D R, Huang K. An indicator of cancer: downregulation of monoamine oxidase-A in multiple organs and species. BMC Genomics. 2008; 9:134.

18. Flamand V, Zhao H, Peehl D M. Targeting monoamine oxidase A in advanced prostate cancer. J Cancer Res Clin Oncol. 2010; 136:1761-71.

19. Yang X, Shi C, Tong R, Qian W, Zhau H E, Wang R, et al. Near IR heptamethine cyanine dye-mediated cancer imaging. Clin Cancer Res. 2010; 16:2833-44.

20. Wu J B, Shao C, Li X, Shi C, Li Q, Hu P, et al. Near-infrared fluorescence imaging of cancer mediated by tumor hypoxia and HIF1α/OATPs signaling axis. Biomaterials. 2014; 35:8175-85.

21. Denko N C. Hypoxia, HIF1 and glucose metabolism in the solid tumour. Nat Rev Cancer. Nature Publishing Group; 2008; 8:705-13.

22. Harris A L. Hypoxia—a key regulatory factor in tumour growth. Nat Rev Cancer. 2002; 2:38-47.

23. Liou G-Y, Storz P. Reactive oxygen species in cancer. Free Radic Res. 2010; 44:479-96.

24. Edmondson D E. Hydrogen peroxide produced by mitochondrial monoamine oxidase catalysis: biological implications. Curr Pharm Des. 2014; 20:155-60.

25. Salgado R, Benoy I, Bogers J, Weytjens R, Vermeulen P, Dirix L, et al. Platelets and vascular endothelial growth factor (VEGF): a morphological and functional study. Angiogenesis. 2001; 4:37-43.

26. Gonzalez F J, Rueda A, Sevilla I, Alonso L, Villarreal V, Torres E, et al. Shift in the balance between circulating thrombospondin-1 and vascular endothelial growth factor in cancer patients: relationship to platelet alpha-granule content and primary activation. Int J Biol Markers. 2004; 19:221-8.

27. Biswas S K, Mantovani A. Macrophage plasticity and interaction with lymphocyte subsets: cancer as a paradigm. Nat Immunol. 2010; 11:889-96.

The invention claimed is:

1. A compound comprising a salt of

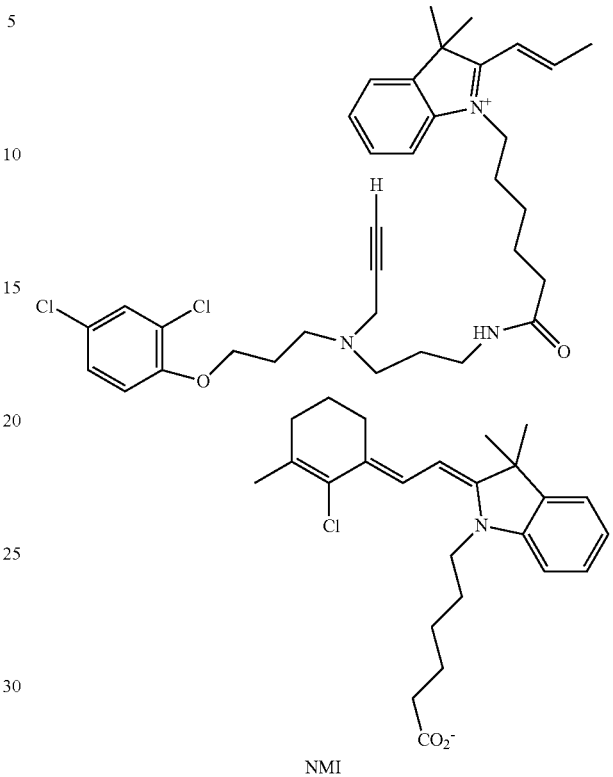

NMI or the carboxylic acid thereof.

2. A pharmaceutical composition comprising the compound of claim 1.

3. The pharmaceutical composition of claim 2 further comprising an excipient.

4. The pharmaceutical composition of claim 2 further comprising a physiologically acceptable carrier.

\* \* \* \* \*